(12) United States Patent
Edelson

(10) Patent No.: US 8,658,391 B2
(45) Date of Patent: Feb. 25, 2014

(54) ASSESSMENT OF THE EFFECTS OF TOPICAL ADMINISTRATION OF CHEMODENERVATING PHARMACEUTICALS

(75) Inventor: Jonathan Edelson, Scarsdale, NY (US)

(73) Assignee: Anterios, Inc., New York, NY (US)

( * ) Notice: Subject to any disclaimer, the term of this patent is extended or adjusted under 35 U.S.C. 154(b) by 1378 days.

(21) Appl. No.: 11/741,125

(22) Filed: Apr. 27, 2007

(65) Prior Publication Data

US 2007/0259391 A1    Nov. 8, 2007

Related U.S. Application Data

(60) Provisional application No. 60/795,449, filed on Apr. 27, 2006.

(51) Int. Cl.
*C12Q 1/46* (2006.01)

(52) U.S. Cl.
USPC .............................. 435/20; 435/19; 424/247.1

(58) Field of Classification Search
None
See application file for complete search history.

(56) References Cited

U.S. PATENT DOCUMENTS

| | | | |
|---|---|---|---|
| 5,008,110 A | 4/1991 | Benecke et al. | |
| 5,401,243 A * | 3/1995 | Borodic | 604/511 |
| 5,591,767 A | 1/1997 | Mohr et al. | |
| 5,683,712 A | 11/1997 | Cavazza | |
| 5,948,433 A | 9/1999 | Burton et al. | |
| 5,965,154 A | 10/1999 | Haralambopoulos | |
| 6,010,715 A | 1/2000 | Wick et al. | |
| 6,087,327 A * | 7/2000 | Pearce et al. | 514/2 |
| 2002/0187164 A1 | 12/2002 | Borodic | |
| 2004/0009180 A1* | 1/2004 | Donovan | 424/184.1 |
| 2005/0175636 A1 | 8/2005 | Donovan | |
| 2006/0182767 A1 | 8/2006 | Borodic | |
| 2012/0164182 A1 | 6/2012 | Edelson et al. | |

FOREIGN PATENT DOCUMENTS

| | | |
|---|---|---|
| EP | 1334729 A1 | 8/2003 |
| WO | WO-9011364 A1 | 10/1990 |
| WO | WO-9639167 A1 | 12/1996 |
| WO | WO 2008070538 A2 * | 6/2008 |

OTHER PUBLICATIONS

Aoki K.R. "Botulinum neurotoxin serotype A and B preparations have different margins in preclinical models of muscle weakening efficacy and systemic safety", Toxicon, 2002, vol. 40, pp. 923-928.*
Johnson E. A. et al. "Clostridium bolulinum neurotoxins—Applications in medicine and potential agents of bioterrorism", Clinical Microbiology Newsletter, Oct. 2005, vol. 27, No. 19, pp. 147-151.*
Carruthers et al., Botulinum A exotoxin use in clinical dermatology, J. Am. Acad. Dermatol. 34(5):788 (1996).
Extended European Search Report for EP07861297.5, 4 pages (Apr. 7, 2010).
Helene et al., Control of Gene Expression by Triple Helix-Forming Oligonucleotides, Ann N.Y. Acad Sci 660:27 (1992).
Helene, The anti-gene strategy: control of gene expression by triplex-forming-oligonucleotides, Anti-Cancer Drug Des 6:569-584 (1991).
International Preliminary Report on Patentability for PCT/US2007/010253, 5 pages (Oct. 28, 2008).
International Search Report for PCT/US2007/010253, 3 pages (Mar. 14, 2008).
Maher, DNA Triple-Helix Formation: An Approach to Artificial Gene Repressors?, BioEssays 14:807 (1992).
Pearce et al., Pharmacologic Characterization of Botulinum Toxin for Basic Science and Medicine, Toxicon 35(9):1373-1412 (1997).
Sarver et al., Ribozymes as Potential Anti-HIV-1 Therapeutic Agents, Science 247:1222-1225 (1990).
Written Opinion for PCT/US2007/010253, 4 pages (Mar. 14, 2008).

* cited by examiner

*Primary Examiner* — Jon P Weber
*Assistant Examiner* — Satyendra Singh
(74) *Attorney, Agent, or Firm* — Choate Hall & Stewart LLP; Brenda Herschbach Jarrell; Atsuko N. Polzin

(57) ABSTRACT

The present invention provides methods for assessing the activity of topically administered chemodenervating agents. In some embodiments, methods for assessing the activity of topically administered chemodenervating agents involve determining the extent of inhibition of acetylcholine release near the site of administration. In some embodiments, methods for assessing activity of topically administered chemodenervating agents involve observing a reflex motion of a limb of a subject.

24 Claims, 4 Drawing Sheets

A

B

ASSESSMENT OF THE EFFECTS OF TOPICAL ADMINISTRATION OF CHEMODENERVATING PHARMACEUTICALS

RELATED APPLICATIONS

The present application is related to and claims priority under 35 U.S.C. 119(e) to U.S. Ser. No. 60/795,449, filed Apr. 27, 2006 (the '449 application); the entire contents of the '449 application are incorporated herein by reference.

BACKGROUND OF THE INVENTION

Many substances exist which are toxic in large doses, but have beneficial effects in smaller doses. For example, when administered at the correct dosage level, chemodenervating agents (e.g. botulinum toxin, tetanus toxin, etc.) can be useful in the treatment of hyperhidrosis, muscular spasm and/or contracture, facial and other wrinkles, headache, etc.

One approach to determining correct dosage levels involves assaying the in vivo activity of chemodenervating agents. U.S. Pat. No. 5,401,243 describes methods for assaying the in vivo activity of injected botulinum toxin. However, no methods have been described for assaying the in vivo activity of topically-administered botulinum toxin. In fact, until very recently, no formulations for topical administration of botulinum toxin have been described. Such topical formulations were recently described in co-pending U.S. patent application Ser. No. 11/607,436, entitled "BOTULINUM NANOEMULSIONS," filed Dec. 1, 2006.

Therefore, there is a need for the development of methods of determining correct dosage levels for topical administration of chemodenervating agents (e.g. botulinum toxin). There is a need for the development of methods of measuring the activity of topically-administered chemodenervating agents in vivo.

SUMMARY OF THE INVENTION

The present invention provides methods for assessing the activity of topically administered chemodenervating agents. In some embodiments, methods for assessing the activity of topically administered chemodenervating agents involve determining the extent of inhibition of acetylcholine release near the site of administration. Inhibition of acetylcholine release is indicative of denervation in a muscle or muscles, therefore the extent of inhibition of acetylcholine release is typically coextensive with the zone of denervation induced by the topically administered chemodenervation agent.

Any chemodenervating agent may be used in accordance with the present invention. Chemodenervating agents are typically substances that are useful in attenuating neural stimulation and/or spasmodic activity of muscle. In some embodiments, a chemodenervating agent is a substance capable of interrupting nerve impulse transmission across a neuromuscular junction in a muscle and/or muscle group. In certain embodiments, chemodenervating agents are neurotoxins (e.g. botulinum toxin, tetanus toxin, etc.). In some embodiments, topically-administered chemodenervating agents include, for example, small molecules (e.g. phenol, alcohol, short-term anesthetics), proteins (including multimeric proteins, protein complexes, etc.), peptides, etc., and/or combinations thereof.

In some embodiments, a chemodenervating agent may be one or more botulinum toxin peptides or protein complexes. In some embodiments, the botulinum toxin may be one or more of botulinum toxin serotypes A, B, $C_1$, $C_2$, D, E, F, or G. In some embodiments, the botulinum toxin may be an isolated and/or purified botulinum toxin. In some embodiments, the botulinum toxin may be a partially-isolated and/or partially-purified botulinum toxin. In some embodiments, the botulinum toxin may be a native botulinum complex. In some embodiments, the botulinum toxin may be associated with non-toxin proteins. In some embodiments, the botulinum toxin may be a recombinantly-made botulinum toxin.

Chemodenervation agent dosage levels that are too high can cause a muscle and/or muscle group to become completely paralyzed, whereas lower dosage levels may only partially or lightly denervate a muscle and/or muscle group. The particular dosages may vary depending on the condition being treated and therapeutic regime being utilized. For example, treatment of subdermal, hyperactive muscles may require high topical dosages (for example, 200 I.U. to 20,000 I.U.) of botulinum toxin. In comparison, treatment of neurogenic inflammation or hyperactive sweat glands may require relatively small topical dosages (for example, about 1 I.U. to about 1,000 I.U.) of botulinum toxin.

Dosage forms for topical administration of a chemodenervating agent may include ointments, pastes, creams, lotions, gels, powders, solutions, sprays, inhalants and/or patches. In some embodiments, pharmaceutical compositions for topical administration of a chemodenervating agent may be in the form of liquid and/or semi liquid preparations such as liniments, lotions, oil-in-water and/or water-in-oil emulsions such as creams, ointments and/or pastes, and/or solutions and/or suspensions. In some embodiments, pharmaceutical compositions for topical administration of a chemodenervating agent may be in the form of microemulsions, nanoemulsions, microparticles, nanoparticles, liposomes, and/or micelles. In some embodiments, pharmaceutical compositions for topical administration of a chemodenervating agent may be in the form of a cosmetic formulation including, but not limited to, a skin softener, nutrition lotion type emulsion, cleansing lotion, cleansing cream, skin milk, emollient lotion, massage cream, emollient cream, make-up base, lipstick, facial pack or facial gel, cleaner formulation (e.g. shampoos, rinses, body cleanser, hair-tonics, or soaps), and dermatological composition (e.g. lotions, ointments, gels, creams, patches or sprays).

Chemodenervating agents such as botulinum toxin act on striated muscle to block release of the acetylcholine neurotransmitter from the presynaptic membrane, resulting in varying degrees of effective denervation of the muscle in regions contacted by the chemodenervating agent. This results in an increase in post-synaptic acetylcholinesterase activity and an increase in the population of acetylcholine receptors, effects which occur as a characteristic physiological response to denervation. Thus, the extent of denervation of a muscle can be determined postmortem by sectioning the muscle and staining for acetylcholinesterase activity using the method of Karnovsky (see, e.g. Woolf et al., *The Innervation of Muscle*, Charles Thomas Pub., Springfield, Ill., 1959).

In some embodiments, the extent of denervation induced by topical administration of a chemodenervating agent to the skin overlying a muscle can be determined by monitoring a reflex motion of a limb of a subject. For example, a reflex motion of a mouse limb can be monitored upon holding the mouse by its tail, and the degree to which the mouse does not raise its limb is measured.

This invention is of practical value for assessing the activity or effectiveness chemodeneravating pharmaceuticals (e.g., botulinum) that may be topically applied to the skin in contrast to prior chemodenervating pharmaceuticals that have been injected subcutaneously or intramuscularly. The invention provides qualitative and/or quantitative methods to assess the magnitude of chemodenervation in muscle that has been pharmacologically treated through the overlying skin with a chemodenervating agent. The invention provides qualitative and/or quantitative methods to assess which specific areas of muscle have been actually chemodenervated through the pharmacologic treatment of the overlying skin with a chemodenervating agent.

The present invention provides methods of standardizing chemodenervating agent-derived pharmaceuticals (e.g. botulinum-derived pharmaceuticals). In some embodiments, the invention provides methods of standardizing chemodenervating agent preparations (e.g. botulinum toxin preparations) with respect to their zone of denervation when topically administered in vivo. In some embodiments, the invention provides mechanisms for testing duration of action and diffusion potential in chemodenervating agent-based preparations (e.g. botulinum toxin preparations). In some embodiments, the invention provides tools for evaluating diffusion potential of various preparations of botulinum-based pharmaceuticals, e.g., various immunotypes, purifications, and formulations. In some embodiments, the invention provides methods for rapid approximation of the denervating effect of a chemodenervating agent.

The invention provides a variety of kits useful for assaying the activity of chemodenervation agents in accordance with the present invention. A kit may comprise one, two, three, or more different substances useful for detecting activity of chemodenervation agents. For example, an inventive kit may include (i) a substance which detects levels of acetylcholinesterase (ACE) in muscle nerve terminals; (ii) a "standard" chemodenervating agent which has a characteristic effect on ACE levels; and (ii) instructions for administering the substance to a subject in order to assay activity of a chemodenervating agent being tested.

This application refers to various patent publications, all of which are incorporated herein by reference.

DEFINITIONS

Figure 1:
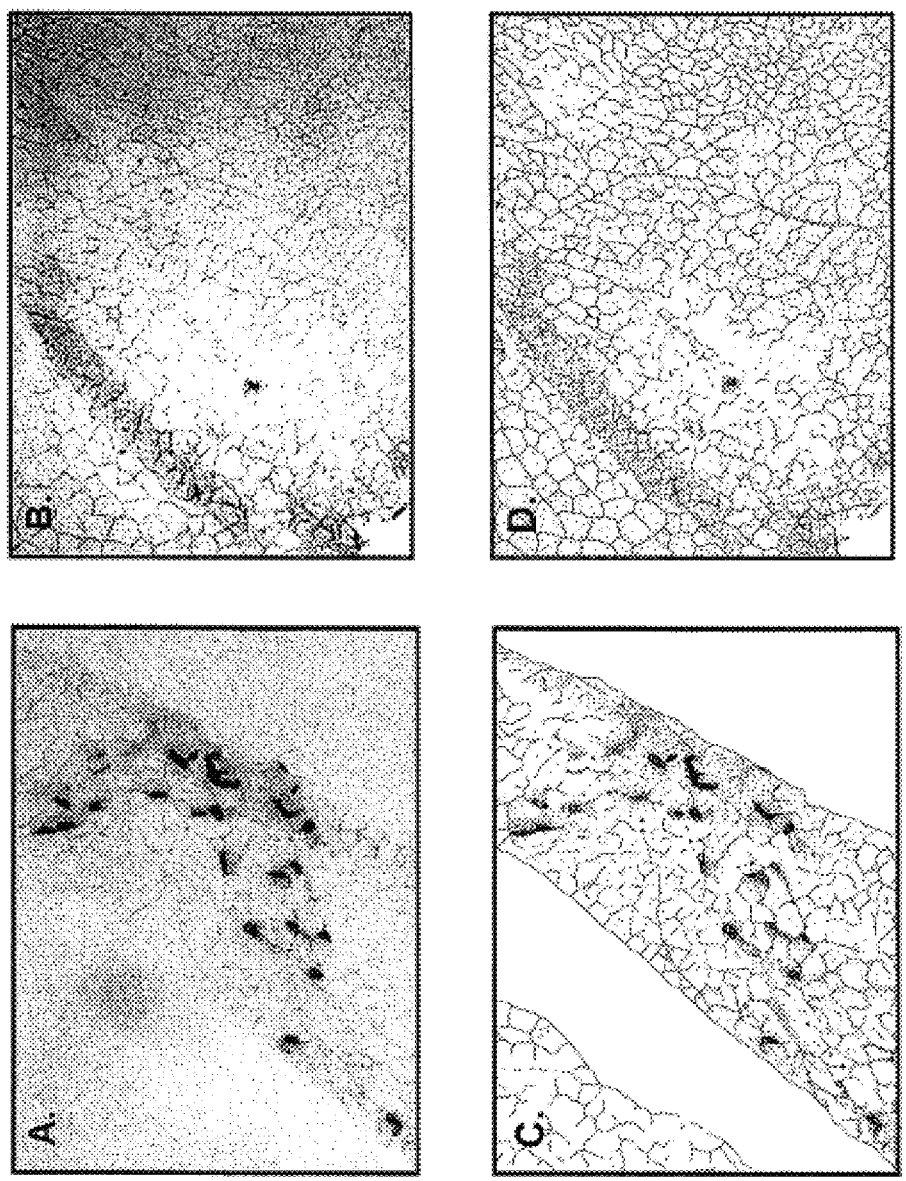
FIG. 1: Effects of topical botulinum on acetylcholine-esterase (ACE) accumulation in muscle tissue. Shown here are ACE tissue stain photomicrographs of mouse bicep muscle tissue, for which skin overlying muscles was treated with (A) topical botulinum preparation containing 0.3 U of Botulinum Type A Toxin Complex admixed in a facial cream ("PCCA Vanishing Cream"), or (B) a negative control preparation containing the identical chemical constituents of the botulinum preparation except the Botulinum Type A Toxin Complex admixed with the same facial cream. The same volume of cream was administered in botulinum-treated (A) and control (B) groups. Photomicrograph (A) shows positive ACE staining of the nerve terminals (innervating the muscle) demonstrating that this muscle was denervated in the pharmacologically treated muscle. Photomicrograph (B) shows negative ACE staining of the nerve terminals (innervating the muscle) demonstrating that the muscle treated with the control preparation was not denervated. (C) and (D) provide illustrations of the photographs shown in (A) and (B), respectively.

Abrasion:

The term "abrasion," as used herein refers to any means of altering, disrupting, removing, or destroying the top layer of the skin. In some embodiments, abrasion refers to a mechanical means of altering, disrupting, removing, or destroying the top layer of the skin. In some embodiments, abrasion refers to a chemical means of altering, disrupting, removing, or destroying the top layer of skin. To give but a few examples, agents such as exfoliants, fine particles (e.g. magnesium or aluminum particles), acids (e.g. alpha-hydroxy acids or beta-hydroxy acids), alcohols, may cause abrasion. In general, permeation enhancers such as those described, for example, by Donovan (e.g. US Publications 2004/009180 and 2005/175636, and PCT Publication WO 04/06954), and Graham (e.g. U.S. Pat. No. 6,939,852 and US Publication 2006/093624), etc., are expected to cause abrasion. Of course, those of ordinary skill in the art will appreciate that a particular agent may cause abrasion when present at one concentration, or in association with one or more other agents, but may not cause abrasion under different circumstances. Thus, whether or not a particular material is an "abrasive agent" depends on context. Abrasion can readily be assessed by those of ordinary skill in the art, for example by observation of redness or irritation of the skin and/or histologic examination of skin showing alteration, disruption, removal, or erosion of the stratum corneum.

Administration:

The term "administration," as used herein to refer to the delivery of an inventive nanoparticle composition to a subject, is not limited to any particular route but rather refers to any route accepted as appropriate by the medical community. For example, the present invention contemplates routes of delivering or administering that include, but are not limited to, transdermal, intramuscular, or subcutaneous. In certain embodiments of the invention, administration is transdermal.

Animal:

As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, genetically-engineered animal, and/or a clone.

Antibody:

As used herein, the term "antibody" refers to an immunoglobulin, whether naturally produced, synthetically produced, or both. The antibody may be a member of any immunoglobulin class, including any of the human classes: IgG, IgM, IgA, IgD, and/or IgE. The antibody may be a fragment of an antibody such as an Fab'; F(ab')$_2$; scFv (single-chain variable) and/or any other fragment that retains an antigen binding site; and/or a recombinantly-produced scFv fragment, including recombinantly-produced fragments (see, e.g., Allen, 2002, *Nat Rev Cancer*, 2:750, and references therein). In certain embodiments of the invention the term refers to "humanized" antibodies, which include sequences of human origin. An antibody may be polyclonal or monoclonal.

Approximately:

As used herein, the term "approximately" or "about," as applied to one or more values of interest, refers to a value that is similar to a stated reference value. In certain embodiments, the terms "approximately" or "about" refer to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less of the stated reference value.

Biologically Active Agent:

As used herein, the phrase "biologically active agent" refers to any substance that has activity in a biological system and/or organism. For instance, a substance that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion. Botulinum toxin is a biologically active agent in accordance with the present invention.

Botulinum Nanoparticle Composition:

The term "botulinum nanoparticle composition," as used herein, refers to any nanoparticle composition in which at least one nanoparticle includes botulinum toxin. The botulinum toxin may be present within the nanoparticle, on the nanoparticle surface and/or within a micellar membrane defining the nanoparticle.

Botulinum Toxin:

The term "botulinum toxin," as used herein, refers to any neurotoxin produced by *Clostridium botulinum*. Except as otherwise indicated, the term encompasses fragments or portions (e.g., the light chain and/or the heavy chain) of such neurotoxin that retain appropriate activity (e.g., muscle relaxant activity). The phrase "botulinum toxin," as used herein, encompasses the botulinum toxin serotypes A, B, C, D, E, F, and G. Botulinum toxin, as used herein, also encompasses both a botulinum toxin complex (i.e., for example, the 300, 600, and 900 kD complexes) as well as the purified (i.e., for example, isolated) botulinum toxin (i.e., for example, about 150 kD). "Purified botulinum toxin" is defined as a botulinum toxin that is isolated, or substantially isolated, from other proteins, including protein that for a botulinum toxin complex. A purified toxin may be greater than 95% pure, and preferably is greater than 99% pure. Those of ordinary skill in the art will appreciate that the present invention is not limited to any particular source of botulinum toxin. For example, botulinum toxin for use in accordance with the present invention may be isolated from *Clostridium botulinum*, may be chemically synthesized, may be produced recombinantly (i.e., in a host cell or organism other than *Clostridium botulinum*), etc.

Chemodenervating Agent:

As used herein, the phrase "chemodenervating agent" refers to any substance that is useful in attenuating neural stimulation and/or spasmodic activity of muscle. In some embodiments, a chemodenervating agent is a substance capable of interrupting nerve impulse transmission across a neuromuscular junction in a muscle and/or muscle group. In certain embodiments, chemodenervating agents are neurotoxins (e.g. botulinum toxin, tetanus toxin, etc.). In particular embodiments, where a protein or polypeptide is a chemodenervating agent, a portion of that protein or polypeptide that shares at least one chemodenervating activity of the protein or polypeptide is typically referred to as a "biologically active" portion.

Cosmeceutical:

The term "cosmeceutical," as used herein, refers to any agent (e.g., for example, benzoyl peroxide or retinol) that possesses both cosmetic and pharmaceutical properties. A cosmeceutical is generally useful for external applications to improve the complexion or overall physical appearance. Cosmeceuticals may be applied as compositions including, but not limited to, creams, oils, foams, sprays, liquids etc. To give but a few examples, carotenoids, phenolic compounds and/or water soluble antioxidants may act as cosmeceuticals.

Cosmetic Formulation:

The term "cosmetic formulation" is used herein to refer to a topically applied composition that contains one or more agents having cosmetic properties. To give but a few examples, a cosmetic formulation may be a skin softener, nutrition lotion type emulsion, cleansing lotion, cleansing cream, skin milk, emollient lotion, massage cream, emollient cream, make-up base, lipstick, facial pack or facial gel, cleaner formulation such as shampoos, rinses, body cleanser, hair-tonics, or soaps, and/or a dermatological composition such as a lotion, ointment, gel, cream, patch and/or spray.

Cream:

The term "cream" refers to a spreadable composition, typically formulated for application to the skin. Creams typically contain an oil and/or fatty acid based-matrix. Creams formulated according to the present invention may contain nanoparticles and may be capable of substantially complete penetration (e.g., of such nanoparticles) through the skin upon topical administration. Such a cream could also act as a carrier for incorporated materials (e.g., for example, for a botulinum toxin).

Dispersion Medium:

The term "dispersion medium" as used herein, refers to a liquid medium in which particles (e.g., nanoparticles) are dispersed. In general, a dispersion is formed when at least two immiscible materials are combined. An "oil-in-water" dispersion is one in which oily particles are dispersed within an aqueous dispersion medium. A "water-in-oil" dispersion is one in which aqueous particles are dispersed within an oily dispersion medium. Those of ordinary skill in the art will appreciate that a dispersion can be formed from any two immiscible media and is not limited strictly to combinations of aqueous and oily media. The term "dispersion medium" therefore applies broadly to any dispersion medium notwithstanding that it is common to refer to "aqueous" and "oily" categories.

Encapsulated:

The term "encapsulated" (also "encapsulate" or "encapsulating") is used herein to mean that the encapsulated entity is completely surrounded by another material. To give but one example, a biologically active agent (e.g., botulinum toxin) may be encapsulated within a nanoparticle in an inventive emulsion. Such encapsulation may be achieved, for example, during formation of a nanoparticle composition (e.g., a nanoemulsion), for example during microfluidization.

In Conjunction with:

As used herein, the phrase delivered "in conjunction with" refers to the co-delivery of two or more things. In particular, according to the present invention, the phrase is used herein in reference to delivery of a biologically active agent with inventive nanoparticles and/or nanoparticle compositions. A substance or agent is delivered in conjunction with nanoparticles when the substance or agent is combined with nanoparticles and/or nanoparticle compositions; is encapsulated or completely surrounded by nanoparticles; is associated with a nanoparticle interface; and/or is adsorbed to the outer surface of a nanoparticle. A substance or agent to be delivered in conjunction with nanoparticles and/or nanoparticle compositions may or may not be covalently linked to the nanoparticles and/or nanoparticle compositions. A substance or agent to be delivered in conjunction with nanoparticles and/or nanoparticle compositions may or may not be attached to the nanoparticles and/or nanoparticle compositions by adsorption forces. In many embodiments of the present invention, the biologically active agent delivered in conjunction with a nanoparticle or nanoparticle composition is botulinum toxin.

Microfluidized:

The term "microfluidized" is generally used herein to describe compositions that have been exposed to high shear force. In some embodiments of the invention, the compositions have been processed by an instrument or a device known as a "microfluidizer." However, in its broadest sense, the term encompasses any composition that has been exposed to high shear force by any means. For example, high shear force may be administered by cavitation or by high pressure homogenization. Alternatively or additionally, high shear force may be administered by exposure to high pressure, for example about 15,000 psi. In some embodiments, such high pressure is within the range of about 18,000 to about 26,000 psi; in some embodiments, it is within the range of about 20,000 to 25,000 psi. As indicated, high shear force may be administered by passage through an instrument such as, for example, a Microfluidizer® Processor (Microfluidics Corporation/MFIC Corporation) or other like device. Microfluidizer® Processors provide high pressure and a resultant high shear rate by accelerating the product through microchannels to a high velocity for size reduction to the nanoscale range. The fluid is split in two and is pushed through microchannels with typical dimensions in the order of 75 microns at high velocities (in the range of 50-300 m/s). As the fluid exits the microchannels it forms jets which collide with jets from opposing microchannels. In the channels the fluid experiences high shear (up to $10^7$ l/s) which is orders of magnitude higher than that of conventional technologies. Jet collisions result in mixing in submicron level. Therefore, high shear and impact are responsible for particle size reduction and mixing of multiphase fluids in the Microfluidizer® technology. In some embodiments of the present invention, a sample is "microfluidized" through exposure to high shear forces for a period of time less than about 10 minutes. In some embodiments, the period of time is less than about 9, 8, 7, 6, 5, 4, 3, 2, or 1 minute(s). In some embodiments, the period of time is within the range of about 1-2 minutes or less; in some embodiments, the period of time is about 30 seconds. In some embodiments of the invention, a sample is "microfluidized" through a single exposure to high shear forces; such embodiments are referred to herein as "single pass" microfluidization.

Nanoemulsion:

An emulsion is traditionally defined in the art "as a system . . . consisting of a liquid dispersed with or without an emulsifier in an immiscible liquid usually in droplets of larger than colloidal size" *Medline Plus Online Medical Dictionary, Merriam Webster* (2005). The term "nanoemulsion," as used herein, refers to an emulsion in which at least some of the droplets (or particles) have diameters in the nanometer size range. As will be understood by those of ordinary skill in the art, a nanoemulsion is characterized by droplets or particles one thousand fold smaller than microemulsion droplets or particles.

Nanoparticle:

As used herein, the term "nanoparticle" refers to any particle having a diameter of less than 1000 nanometers (nm). In some embodiments, a nanoparticle has a diameter of less than 300 nm, as defined by the National Science Foundation. In some embodiments, a nanoparticle has a diameter of less than 100 nm as defined by the National Institutes of Health. Those of ordinary skill in the art will appreciate that, the term "nanoparticle" as used herein describes the dispersed phase in a dispersion or emulsion.

Nanoparticle Composition:

As used herein, the term "nanoparticle composition" refers to any composition that includes at least one nanoparticle. In some embodiments, a nanoparticle composition is a uniform collection of nanoparticles. Nanoparticle compositions described herein are typically emulsions or dispersions. In some embodiments, a nanoparticle composition is stable. In some embodiments, a nanoparticle composition includes one or more biologically active agents to be delivered in conjunction with the nanoparticles. In some embodiments, the nanoparticle composition is a nanoemulsion. It will be appreciated by those of ordinary skill in the art that a nanoparticle composition may be prepared according to any available means including, for example, chemical or mechanical means. In some embodiments of the present invention, a nanoparticle composition is prepared by subjecting a sample to microfluidization. In some embodiments of the invention, a nanoparticle composition is prepared without use of toxic solvents and/or is substantially free of toxic solvents.

Not Contaminated with:

The phrase "not contaminated with," when used herein to refer to a nanoparticle composition, is synonymous with "substantially free of" and describes a nanoparticle composition containing no more than about 50% of the recited material. For example, if a nanoparticle composition is said to be "substantially free of" particles whose diameter is outside of a stated range, then no more than about 50% of the particles in that composition have diameters outside of the range. In some embodiments, no more than 25% of the particles are outside of the range. In some embodiments, no more than 20%, 19%, 18%, 17%, 16%, 15%, 14%, 13%, 12%, 10%, 9%, 8%, 7%, 6%, 5%, 4%, 3%, 2%, 1%, 0.5% or less of the particles have diameters outside of the stated range.

Nucleic Acid:

As used herein, the term "nucleic acid," in its broadest sense, refers to any compound and/or substance that can be incorporated into an oligonucleotide chain. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns.

Pharmaceutically Acceptable:

The term "pharmaceutically acceptable" as used herein, refers to agents that, within the scope of sound medical judgment, are suitable for use in contact with the tissues of human beings and animals without excessive toxicity, irritation, allergic response, or other problem or complication, commensurate with a reasonable benefit/risk ratio.

Premix:

The term "premix" as used herein, refers to any combination of components that is subsequently used to generate a nanoparticle composition or according to the present invention. For example, a premix is any collection of ingredients that, when subjected to high shear force, generates nanoparticles according to the present invention. In some embodiments, a premix is a collection of ingredients that, when subjected to high shear force, generates a nanoparticle composition such as a uniform nanoparticle composition. A premix often contains a liquid dispersion medium and other components sufficient to generate nanoparticles within the dispersion medium. According to the present invention, botulinum toxin may also be included in the premix. The premix may also contain one or more surfactants and/or other agents. In some embodiments, the premix constitutes a solution. In some particular embodiments in which the premix includes botulinum toxin and/or another biologically active agent, the botulinum toxin (and/or other biologically active agent) is in solution before high shear force is applied to the premix.

Protein:

As used herein, a "protein" generally refers to a polypeptide (i.e., a string of at least two amino acids linked to one another by peptide bonds). Proteins may include moieties other than amino acids (e.g., may be glycoproteins) and/or may be otherwise processed or modified. Those of ordinary skill in the art will appreciate that a "protein" can be a complete polypeptide chain as produced by a cell (with or without a signal sequence) or can be a functional portion thereof. Those of ordinary skill will appreciate that a protein can sometimes include more than one polypeptide chain, for example linked by one or more disulfide bonds or associated by other means.

Small Molecule:

In general, a "small molecule" is understood in the art to be an organic molecule that is less than about 5 kilodaltons (Kd) in size. In some embodiments, the small molecule is less than about 3 Kd, 2 Kd, or 1 Kd. In some embodiments, the small molecule is less than about 800 daltons (D), 600 D, 500 D, 400 D, 300 D, 200 D, or 100 D. In some embodiments, small molecules are non-polymeric. In some embodiments, small molecules are not proteins, peptides, or amino acids. In some embodiments, small molecules are not nucleic acids or nucleotides. In some embodiments, small molecules are not saccharides or polysaccharides.

Stable:

The term "stable," when applied to nanoparticle compositions herein, means that the compositions maintain one or more aspects of their physical structure (e.g., size range and/or distribution of particles) over a period of time. In some embodiments of the invention, a stable nanoparticle composition is one for which the average particle size, the maximum particle size, the range of particle sizes, and/or the distribution of particle sizes (i.e., the percentage of particles above a designated size and/or outside a designated range of sizes) is maintained for a period of time. In some embodiments, the period of time is at least about one hour; in some embodiments the period of time is about 5 hours, 10 hours, one (1) day, one (1) week, two (2) weeks, one (1) month, two (2) months, three (3) months, four (4) months, five (5) months, six (6) months, eight (8) months, ten (10) months, twelve (12) months, twenty-four (24) months, or longer. In some embodiments, the period of time is within the range of about one (1) day to twenty-four (24) months, two (2) weeks to twelve (12) months, two (2) months to five (5) months, etc. For example, if a population of nanoemulsion particles is subjected to prolonged storage, temperature changes, and/or pH changes and a majority of the nanoparticles in the population maintain a diameter within a stated range (i.e., for example, between approximately 10-120 nm), the nanoemulsion is stable. For some such populations, a majority is more than about 50%, 60%, 70%, 80%, 90%, 95%, 96%, 97%, 98%, 99%, 99.5%, 99.6%, 99.7%, 99.8%, 99.9% or more. In some embodiments of the invention, where a nanoparticle composition comprises botulinum toxin and/or at least one other biologically active agent, the nanoparticle composition is considered stable if the concentration of biologically active agent (e.g., botulinum toxin) is maintained in the composition over the designated period of time under a designated set of conditions.

Subject:

The term "subject" or "patient," as used herein, refers to any animal to which an inventive nanoparticle composition may be delivered or administered. For example, a subject may be a human, dog, cat, cow, pig, horse, mouse, rat, gerbil, hamster etc. In many embodiments of the present invention, the subject is a human.

Therapeutically Effective Amount:

As used herein, the term "therapeutically effective amount" means an amount that is sufficient, when administered to an individual suffering from or susceptible to a disease, disorder, and/or condition, to treat the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response when administered or delivered to a significant number of subjects in need of such treatment. It is specifically understood that particular subjects may, in fact, be "refractory" to a "therapeutically effective amount." To give but one example, a refractory subject may have a low bioavailability such that clinical efficacy is not obtainable. In some embodiments, reference to a therapeutically effective amount may be a reference to an amount as measured in one or more specific tissues.

Toxic Solvent:

As used herein, the term "toxic solvent" refers to any substance that may alter, disrupt, remove, or destroy an animal's tissue. As would be understood by one of ordinary skill in the art, an animal's tissue can include living cells, dead cells, extracellular matrix, cellular junctions, biological molecules, etc. To give but a few examples, toxic solvents include dimethyl sulfoxide, dimethyl acetimide, dimethyl foramide, chloroform, tetramethyl foramide, acetone, acetates, and alkanes.

Treatment:

As used herein, the term "treatment" (also "treat" or "treating") refers to any administration of a biologically active agent that partially or completely alleviates, ameliorates, relives, inhibits, delays onset of, reduces severity of and/or reduces incidence of one or more symptoms or features of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

Uniform:

The term "uniform," when used herein in reference to a nanoparticle composition, refers to a nanoparticle composition in which the individual nanoparticles have a specified range of particle diameter sizes. For example, in some embodiments, a uniform nanoparticle composition is one in which the difference between the minimum diameter and maximum diameter does not exceed approximately 600, 550, 500, 450, 400, 350, 300, 250, 200, 150, 100, 90, 80, 70, 60, 50, or fewer nm. In some embodiments, particles (e.g., botulinum-toxin-containing particles) within inventive uniform botulinum nanoparticle compositions have diameters that are smaller than about 600, 550, 500, 450, 400, 350, 300, 250, 200, 150, 130, 120, 115, 110, 100, 90, 80 nm, or less. In some embodiments, particles (e.g., botulinum-toxin-containing particles) within inventive uniform botulinum nanoparticle compositions have diameters within the range of about 10 and about 600 nanometers. In some embodiments, particles within inventive uniform botulinum nanoparticle compositions have diameters within the range of about 10-300, 10-200, 10-150, 10-130, 10-120, 10-115, 10-110, 10-100, or 10-90 nm. In some embodiments, particles (e.g., botulinum-toxin-containing particles) within inventive botulinum nanoparticle compositions have an average particle size that is under about 300, 250, 200, 150, 130, 120, or 115, 110, 100, or 90 nm. In some embodiments, the average particle size is within the range of about 10-300, 50-250, 60-200, 65-150, 70-130 nm. In some embodiments, the average particle size is about 80-110 nm. In some embodiments, the average particle size is about 90-100 nm. In some embodiments, a majority of the particles (e.g., botulinum-toxin-containing particles) within inventive uniform nanoparticle compositions have diameters below a specified size or within a specified range. In some embodiments, the majority is more than 50%, 60%, 70%, 75%, 80%, 85%, 90%, 95%, 96%, 97%, 98%, 99%, 99.5%, 99.6%, 99.7%, 99.8%, 99.9% or more of the particles in the composition. In some embodiments of the invention, a uniform nanoparticle composition is achieved by microfluidization of a sample.

DESCRIPTION OF CERTAIN PREFERRED EMBODIMENTS

The present invention provides methods for assessing the activity of topically administered chemodenervating agents. In some embodiments, methods for assessing the activity of topically administered chemodenervating agents involve determining the extent of inhibition of acetylcholine release near the site of administration. In some embodiments, methods for assessing activity of topically administered chemodenervating agents involve observing a reflex motion of a limb of a subject.

Chemodenervating Agents

Any chemodenervating agent may be used in accordance with the present invention. Chemodenervating agents are typically substances that are useful in attenuating neural stimulation and/or spasmodic activity of muscle. In some embodiments, a chemodenervating agent is a substance capable of interrupting nerve impulse transmission across a neuromuscular junction in a muscle and/or muscle group. In certain embodiments, chemodenervating agents are neurotoxins (e.g. botulinum toxin, tetanus toxin, tetrodotoxin, etc.).

In some embodiments, topically-administered chemodenervating agents include, for example, small molecules, proteins (including multimeric proteins, protein complexes, etc.), peptides, antibodies, nucleic acids, etc., and/or combinations thereof. Relevant chemodenervating agents can be produced or obtained according to any available method or approach.

In some embodiments, a chemodenervating agent may be a small molecule and/or organic compound with pharmaceutical activity. In some embodiments, small molecule chemodenervating agents include phenol, alcohol, and/or short-term anesthetics (e.g. lidocaine, xylocalne, etc.), etc.

In some embodiments, a chemodenervating agent may be a protein. As used herein, the terms "protein" and "peptide" can be used interchangeably. In certain embodiments, peptides range from about 5 to 40, 10 to 35, 15 to 30, or 20 to 25 amino acids in size. Peptides from panels of peptides comprising random sequences and/or sequences which have been varied consistently to provide a maximally diverse panel of peptides may be used.

In some embodiments, a chemodenervating agent may be a neurotoxin (e.g. botulinum toxin, tetanus toxin, etc.). However, any substance which interrupts neuromuscular transmission at the synapse may be used in accordance with the present invention. Thus, it is contemplated that other substances, biologically active portions, recombinantly-produced materials, and other various novel types of pharmaceutical preparations can be used in accordance with the present invention.

In some embodiments, a chemodenervating agent may be one or more botulinum toxin peptides or protein complexes. In some embodiments, the botulinum toxin may be one or more of botulinum toxin serotypes A, B, $C_1$, $C_2$, D, E, F, or G. In some embodiments, the botulinum toxin may be an isolated and/or purified botulinum toxin. In some embodiments, the botulinum toxin may be a partially-isolated and/or partially-purified botulinum toxin. In some embodiments, the botulinum toxin may be a native botulinum complex. In some embodiments, the botulinum toxin may be associated with non-toxin proteins. In some embodiments, the botulinum toxin may be a recombinantly-made botulinum toxin.

In some embodiments, a chemodenervating agent may be an antibody. In some embodiments, antibodies may include, but are not limited to, polyclonal, monoclonal, chimeric (i.e. "humanized"), single chain (recombinant) antibodies. In some embodiments, antibodies may have reduced effector functions and/or bispecific molecules. In some embodiments, antibodies may include Fab fragments and/or fragments produced by a Fab expression library.

In some embodiments, a chemodenervating agent may be a nucleic acid. In some embodiments, oligonucleotides comprise DNA, RNA, chimeric mixtures, derivatives, characteristic portions, and/or modified versions thereof. Oligonucleotides to be used in accordance with the present invention may be single-stranded and/or double-stranded. An oligonucleotide may be modified at the base moiety, sugar moiety, and/or phosphate backbone, for example, to improve stability of the molecule, hybridization, etc.

In some embodiments, a nucleic acid chemodenervating agent comprises an antisense molecule that binds to a translational start site, transcriptional start site, and/or splice junctions. Antisense oligonucleotides will bind to a target mRNA and/or prevent translation. Alternatively or additionally, an antisense oligonucleotide may bind to DNA of a target gene, such as, for example, a regulatory element.

In some embodiments, a nucleic acid chemodenervating agent comprises a ribozyme designed to catalytically cleave target mRNA transcripts may be used to prevent translation of a target mRNA and/or expression of a target (see, e.g., PCT publication WO 90/11364; and Sarver et al., 1990, *Science* 247:1222). Alternatively or additionally, endogenous target gene expression may be reduced by targeting deoxyribonucleotide sequences complementary to the regulatory region of the target gene (i.e., the target gene's promoter and/or enhancers) to form triple helical structures that prevent transcription of the target gene in target muscle cells in the body (see generally, Helene, 1991, *Anticancer Drug Des.* 6:569; Helene et al., 1992, *Ann, N.Y. Acad. Sci.* 660:27; and Maher, 1992, Bioassays 14:807).

Chemodenervating agents for topical delivery may be a mixture of chemodenervating agents. For example, botulinum toxin may be delivered in combination with a small molecule chemodenervating agent such as phenol. In some embodiments, "in combination with" is intended to mean that the components are administered together as part of the same formulation. In some embodiments, "in combination with" is intended to mean that the components are administered separately to the same patient as part of a therapeutic regime (for example, phenol may be administered to large muscles, whereas botulinum toxin may be separately administered to smaller muscles).

Those skilled in the art will recognize that this is an exemplary, not comprehensive, list of chemodenervating agents. Activity of any chemodenervating agent may be assayed in accordance with the present invention.

Chemodenervating agents may be used to treat a spectrum of diseases, such as hyperhidrosis; muscular spasm and/or contracture (e.g. various forms of palsy, facial contracture, dystonia, hemifacial spasm, tremor, spasticity (e.g. resulting from multiple sclerosis), retroorbital muscle, various other ophthalmologic conditions, etc. (Carruthers et al., 1996, *J. Am. Acad. Dermatol.,* 34:788)); facial wrinkles (e.g. glabellar wrinkles, facial lines (e.g. hyperkinetic facial lines), forehead frown lines, midfacial wrinkles, mouth wrinkles, neck lines and banding (e.g. platysma bands), and chin creases); facial dyskinesis (e.g., Meige syndrome, hemifacial spasm, aberrant regeneration of facial nerves, apraxia of eyelid opening, etc.); jaw dystonia, occupational dystonia; corneal ulceration; spasmodic dystonia; headache; and/or prostate hyperplasia.

Dosage

Chemodenervation agent dosage levels that are too high can cause a muscle and/or muscle group to become completely paralyzed, whereas lower dosage levels may only partially or lightly denervate a muscle and/or muscle group. Topical administration of a sublethal dose of a neurotoxin to skin overlying a muscle and/or muscle group results in intramuscular delivery of the neurotoxin, which diffuses outwardly to a distance that is a complex function of the identity and amount of diluent if any administered with the neurotoxin; the mass of the neurotoxin; the population of presynaptic receptors about the site of administration; and/or the current physiological condition of the patient. Diffusion, driven presumably by the concentration gradient, slows as active neurotoxin binds to receptors on the presynaptic membrane. Some portion of the neurotoxin is swept away by the vascular system and distributed systemically. Some other portion may be proteolytically degraded before binding. In some embodiments, energy (e.g., electricity, ultrasound, electromagnetic, etc.) is used to facilitate transdermal penetration of a chemodenervating agent. The type, amount, and duration of energy could all affect the degree of chemodenervation, and the degree of chemodenervation can be assessed. In some embodiments, mechanical or chemical disruption of one or more of the upper layers of the skin (e.g., stratum corneum) is used to facilitate transdermal penetration of a chemodenervating agent. The type, amount, and duration of such disruption could affect the degree of chemodenervation, and the degree of chemodenervation can be assessed.

Topical administration of a therapeutically effective amount of a chemodenervating agent results in paralysis of a subset of the neuromuscular junctions innervating the muscle but leaves others in a functioning state. Chemodenervating agent (e.g. neurotoxin) preparations may be quantified by measuring the $LD_{50}$ in white mice following injection (e.g., intraperitoneally) into the mice. $LD_{50}$ in white mouse equals one international unit or I.U. In some embodiments, dosage levels are between 1 I.U. and 20,000, between 1 I.U. and 15,000, between 1 I.U. and 10,000, between 1 I.U. and 5000, between 1 I.U. and 1000, between 1 I.U. and 750 I.U., between 1 I.U. and 500 I.U., between 1 I.U. and 250 I.U., or between 1 I.U. and 100 I.U administered to the skin overlying a muscle and/or muscle group. In some embodiments, dosage levels are less than 20,000 I.U., less than 15,000 I.U., less than 10,000 I.U., less than 5000 I.U., less than 1000 I.U., less than 900 I.U., less than 800 I.U., less than 700 I.U., less than 600 I.U., less than 500 I.U., less than 400 I.U., less than 300 I.U., less than 200 I.U., less than 100 I.U., or less than 50 I.U. administered to the skin overlying a muscle and/or muscle group. In some embodiments, dosage levels are approximately 20,000 I.U., approximately 15,000 I.U., approximately 10,000 I.U., approximately 5000 I.U., approximately 1000 I.U., approximately 900 I.U., approximately 800 I.U., approximately 700 I.U., approximately 600 I.U., approximately 500 I.U., approximately 400 I.U., approximately 300 I.U., approximately 200 I.U., approximately 100 I.U., approximately 50 I.U., or approximately 25 I.U. administered to the skin overlying a muscle and/or muscle group.

The particular dosages may vary depending on the condition being treated and therapeutic regime being utilized. For example, treatment of subdermal, hyperactive muscles may require high topical dosages (for example, 200 I.U. to 20,000 I.U.) of botulinum toxin. In comparison, treatment of neurogenic inflammation or hyperactive sweat glands may require relatively small topical dosages (for example, about 1 I.U. to about 1,000 I.U.) of botulinum toxin. In some embodiments, the composition may comprise an amount of botulinum toxin sufficient to achieve a therapeutic effect lasting between 1 month and 5 years. In some embodiments, the composition comprising botulinum toxin may be formulated to avoid potential complications including, but not limited to, systemic toxicity or botulism poisoning.

In certain embodiments, botulinum toxin within a composition for topical administration may be present in an amount so that between about $10^{-3}$ I.U./kg and 10 I.U./kg pass through a subject's skin. In some embodiments, botulinum toxin may be present in an amount so that between about $10^{-2}$ I.U./kg and about 1 I.U./kg pass through a subject's skin. In some embodiments, the botulinum toxin may be present in an amount so that between about $10^{-1}$ I.U./kg and about 1 I.U./kg pass through a subject's skin. In some embodiments, the botulinum toxin may be present in an amount so that between about 0.1 I.U. and about 5 I.U. pass through a subject's skin. In some embodiments, botulinum toxin may be present in an amount so that between about 5 I.U. and about 25 I.U. pass through a subject's skin. In some embodiments, botulinum toxin may be present in an amount so that between about 25 I.U. and about 100 I.U. pass through a subject's skin. In some embodiments, botulinum toxin may be present in an amount so that between about 100 I.U. and about 250 I.U. pass through a subject's skin.

Administration of Chemodenervation Agents

Dosage forms for topical administration of a chemodenervating agent may include ointments, pastes, creams, lotions, gels, powders, solutions, sprays, inhalants and/or patches. Generally, the chemodenervating agent is admixed under sterile conditions with a pharmaceutically acceptable carrier and/or any needed preservatives and/or buffers as may be required. General considerations in the formulation and/or manufacture of pharmaceutical agents may be found, for example, in *Remington: The Science and Practice of Phar-*

*macy* 21$^{st}$ ed., Lippincott Williams & Wilkins, 2005. Alternatively or additionally, chemodenervating agents may be topically administered using transdermal patches, which often have the added advantage of providing controlled delivery of a substance to a subject. Such dosage forms may be prepared, for example, by dissolving and/or dispensing the compound in the proper medium. Alternatively or additionally, the rate may be controlled by either providing a rate controlling membrane and/or by dispersing the compound in a polymer matrix and/or gel.

In some embodiments, pharmaceutical compositions for topical administration of a chemodenervating agent may be in the form of liquid and/or semi liquid preparations such as liniments, lotions, oil-in-water and/or water-in-oil emulsions such as creams, ointments and/or pastes, and/or solutions and/or suspensions. In some embodiments, pharmaceutical compositions for topical administration of a chemodenervating agent may be in the form of microemulsions, nanoemulsions, microparticles, nanoparticles, liposomes, and/or micelles. In some embodiments, pharmaceutical compositions for topical administration of a chemodenervating agent are described in co-pending U.S. Patent Application 60/872,198, entitled "AMPHIPHILIC ENTITY NANOPARTICLES," and Ser. No. 11/607,436, entitled "BOTULINUM NANOEMULSIONS," both filed on Dec. 1, 2006. In some embodiments, topically-administrable formulations may comprise from about $1\times10^{-8}\%$ to about 10%, from about $1\times10^{-7}\%$ to about 10%, from about $1\times10^{-6}\%$ to about 10%, from about $1\times10^{-5}\%$ to about 10%, from about $1\times10^{-4}\%$ to about 10%, from about 0.001% to about 10%, from about 0.01% to about 10%, from about 0.1% to about 10%, or from about 1.0% to about 10% (w/w) active ingredient. In some embodiments, topically-administrable formulations may comprise from about $1\times10^{-8}\%$ to about 1.0%, from about $1\times10^{-8}\%$ to about 0.1%, from about $1\times10^{-8}\%$ to about 0.01%, from about $1\times10^{-8}\%$ to about 0.001%, from about $1\times10^{-8}\%$ to about $1\times10^{-4}\%$, from about $1\times10^{-8}\%$ to about $1\times10^{-5}\%$, from about $1\times10^{-8}\%$ to about $1\times10^{-6}\%$, or from about $1\times10^{-8}\%$ to about $1\times10^{-7}\%$ (w/w) active ingredient. In some embodiments, topically-administrable formulations may comprise about $1\times10^{-8}\%$, about $1\times10^{-7}\%$, about $1\times10^{-6}\%$, about $1\times10^{-5}\%$, about $1\times10^{-4}\%$, about 0.001%, about 0.01%, about 0.1%, about 1.0%, or about 10% (w/w) active ingredient. In some embodiments, the concentration of the active ingredient may be as high as the solubility limit of the active ingredient in the solvent. Formulations for topical administration may further comprise one or more of the additional ingredients described herein.

In some embodiments, pharmaceutical compositions for topical administration of a chemodenervating agent may be in the form of a cosmetic formulation including, but not limited to, a skin softener, nutrition lotion type emulsion, cleansing lotion, cleansing cream, skin milk, emollient lotion, massage cream, emollient cream, make-up base, lipstick, facial pack or facial gel, cleaner formulation (e.g. shampoos, rinses, body cleanser, hair-tonics, or soaps), and dermatological composition (e.g. lotions, ointments, gels, creams, patches or sprays).

In some embodiments, a composition for topical administration of a chemodenervating agent may be in the form of a transdermal patch. The use of adhesive patches is well known in the art (for example, see U.S. Pat. 296,006 (design); U.S. Pat. Nos. 6,010,715; 5,591,767; 5,008,110; 5,683,712; 5,948,433; and 5,965,154). In some embodiments, a transdermal patch may comprise an adhesive layer, which may be applied to a subject's skin. In some embodiments, a transdermal patch may comprise a depot or reservoir for holding a chemodenervating agent. In some embodiments, a transdermal patch comprises an exterior surface that may prevent leakage of the chemodenervating agent from the depot. In some embodiments, the exterior surface of a patch may be non-adhesive.

In some embodiments, a composition for topical administration of a chemodenervating agent may be incorporated into a patch so that the chemodenervating agent remains stable for extended periods of time. A chemodenervating agent may be incorporated into a polymeric matrix that stabilizes the chemodenervating agent and permits the chemodenervating agent to diffuse from the matrix and from the patch. In some embodiments, a chemodenervating agent may be incorporated into the adhesive layer of the patch. In some embodiments, the adhesive layer may be heat-activated. In certain embodiments, temperatures of about 37° C. may cause the adhesive to slowly liquefy so that the chemodenervating agent diffuses through the skin. In certain embodiments, the adhesive may remain tacky when stored at less than 37° C. In some embodiments, the adhesive loses its tackiness as it liquefies at temperatures of about 37° C. In some embodiments, the administration of the chemodenervating agent is complete once the patch no longer adheres to the skin.

In some embodiments, a device may be employed that allows the composition to be applied without first applying the composition to one's fingers, which may lead to undesirable paralysis of the fingers. Suitable devices include spatulas, swabs, syringes without needles, and adhesive patches. Use of spatulas or swabs, or the like may require the device to be inserted into a container containing the composition. Using syringes or adhesive patches may be accomplished by filling the syringe or patch with the composition. The chemodenervating agent may be topically spread by the spatulas or swabs, or may be expelled from the syringes onto a subject's skin.

Botulinum Toxin Biology

Botulinum toxin (BTX) BTX is produced in nature by the anaerobic, gram positive bacterium *Clostridium botulinum* and is a potent polypeptide neurotoxin. Most notably, BTX causes a neuroparalytic illness in humans and animals referred to as botulism. BTX can apparently pass untenanted through the lining of the gut and attack peripheral motor neurons. Symptoms of botulinum toxin intoxication can progress from difficulty walking, swallowing, and speaking to paralysis of the respiratory muscles, and death.

BTX-A is the most lethal natural biological agent known to man. The $LD_{50}$ in female Swiss Webster mice (18-20 g) for commercially available BTX-A is about 50 picograms; this amount is defined as 1 Unit of BTX-A. On a molar basis, BTX-A is about 1.8 billion times more lethal than diphtheria, about 600 million times more lethal than sodium cyanide, about 30 million times more lethal than cobra toxin and about 12 million times more lethal than cholera (Singh, et al., ed., "Critical Aspects of Bacterial Protein Toxins" *Natural Toxins II*, pp. 63-84, Plenum Press, New York, 1996).

The different serotypes of botulinum toxin vary in the animal species that they affect and in the severity and duration of the paralysis they evoke. For example, it has been determined that BTX-A is 500 times more potent than is BTX-B, as measured by the rate of paralysis produced in the rat. Additionally, BTX-B has been determined to be non-toxic in primates at a dose of 480 U/kg, which is about 12 times the primate $LD_{50}$ for BTX-A. Furthermore, it is known that botulinum toxin type B has, upon intramuscular injection, a shorter duration of activity and is also less potent than BTX-A at the same dose level.

Botulinum toxin apparently binds with high affinity to cholinergic motor neurons, is translocated into the neuron and blocks the release of acetylcholine.

Botulinum toxins have been used in clinical settings for the treatment of certain neuromuscular disorders. In particular, BTX-A has been approved by the U.S. Food and Drug Administration for the treatment of blepharospasm, strabismus, and hemifacial spasm. Non-type A botulinum toxin serotypes apparently have a lower potency and/or a shorter duration of activity as compared to BTX-A. Clinical effects of peripheral intramuscular BTX-A are usually seen within one week of injection. The typical duration of symptomatic relief from a single intramuscular injection of BTX-A averages about three months.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kilodalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes. Significantly, it is known that the cytosol of pancreatic islet B cells contains at least SNAP-25 (Biochem J 1; 339 (pt 1): 159-65 (April 1999)), and synaptobrevin (Mov Disord 1995 May; 10(3): 376).

The molecular weight of the botulinum toxin protein molecule, for all seven of the known botulinum toxin serotypes, is about 150 kD. Interestingly, the botulinum toxins are released by *Clostridial* bacterium as complexes comprising the 150 kD botulinum toxin protein molecule along with associated non-toxin proteins. Thus, the BTX-A complex can be produced by *Clostridial* bacterium as 900 kD, 500 kD and 360 kD forms. Botulinum toxin types B and $C_1$ are apparently produced as only a 500 kD complex. Botulinum toxin type D is produced as both 300 kD and 500 kD complexes. Finally, botulinum toxin types E and F are produced as only approximately 300 kD complexes.

The BTX complexes (i.e., those compositions having molecular weights greater than about 150 kD) are believed to contain a non-toxin hemagglutinin protein and a non-toxin and non-toxic non-hemagglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

Either BTX proteins or BTX complexes may be utilized in accordance with the present invention. Indeed, it will be appreciated by those of ordinary skill in the art that any portion or fragment of a BTX protein or complex that retains the appropriate activity may be utilized as described herein.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP and glutamate.

As noted above, the source of botulinum toxin is not critical to the present invention. For purposes of completeness, however, we note that a variety of sources, including commercial sources, for certain botulinum toxin preparations are readily available.

For example, BTX or BTX complex can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the BTX-A serotype typically only cleave a portion of the toxin produced. The exact proportion of nicked to unnicked molecules can depend on the length of incubation and the temperature of the culture. Therefore, a certain percentage of any preparation of, for example, the BTX-A toxin is likely to be inactive. The presence of inactive botulinum toxin molecules in a clinical preparation will contribute to the overall protein load of the preparation, which has been linked in some commercially available botulinum toxin preparations to increased antigenicity, without contributing to its clinical efficacy.

High quality crystalline botulinum toxin type A can be produced from the Hall A strain of *Clostridium botulinum* with characteristics of $>3\times10^7$ U/mg, an $A_{260}/A_{278}$ of less than 0.60 and a distinct pattern of banding on gel electrophoresis. The known Schantz process can be used to obtain crystalline botulinum toxin including type A (Shantz et al., 1992, *Microbiol. Rev.*, 56:80).

Generally, the botulinum toxin complex can be isolated and purified from an anaerobic fermentation by cultivating *Clostridium botulinum* (e.g., type A) in a suitable medium. The known process can be used, upon separation out of the non-toxin proteins, to obtain pure botulinum toxins, such as for example: purified botulinum toxin type A with an approximately 150 kD molecular weight with a specific potency of 1-2×10$^8$ LD$_{50}$ U/mg or greater; purified botulinum toxin type B with an approximately 156 kD molecular weight with a specific potency of 1-2×10$^8$ LD$_{50}$ U/mg or greater, and; purified botulinum toxin type F with an approximately 155 kD molecular weight with a specific potency of 1-2×10$^7$ LD$_{50}$ U/mg or greater.

Alternatively or additionally, already prepared and purified botulinum toxins and toxin complexes can be obtained from, for example, List Biological Laboratories, Inc., Campbell, Calif.; the Centre for Applied Microbiology and Research, Porton Down, U.K.; Wako (Osaka, Japan) as well as from Sigma Chemicals of St Louis, Mo.

Pure botulinum toxin, when administered as a free solution, is so labile that it is generally not used to prepare a pharmaceutical composition. Furthermore, the botulinum toxin complexes, such the toxin type A complex can also be susceptible to denaturation due to surface denaturation, heat, and alkaline conditions. In some cases, inactivated toxin forms toxoid proteins which may be immunogenic. Resulting antibodies can render a patient refractory to toxin injection.

In some embodiments, the present invention provides botulinum toxin nanoparticle compositions (e.g., nanoemulsions) in which the botulinum toxin has improved stability when compared to currently administered free solutions. That is, in some embodiments, botulinum toxin present in an inventive nanoparticle composition is protected, at least in part, from at least one adverse condition such as heat, alkaline conditions, acidic conditions, degradative enzymes, host organism antibodies, etc. Alternatively or additionally, botulinum toxin present in inventive nanoparticle compositions may show less surface denaturation than an otherwise comparable preparation of botulinum toxin in free solution. To give but one specific example, 50 picograms a botulinum toxin within a microfluidized nanoemulsion according to the present invention will be protected from certain adverse conditions, etc that may result in surface denaturation.

Indeed, one aspect of the present invention encompasses the recognition that botulinum toxin may be stabilized by incorporation into a nanoparticle composition. Those of ordinary skill in the art will readily appreciate that a nanoparticle composition according to this aspect of the present invention may be prepared by any available means.

The present invention further provides botulinum toxin nanoparticle compositions (e.g., nanoemulsions) in which the botulinum toxin has improved ability to permeate skin when compared to currently administered free solutions. For example, botulinum toxin incorporated within a microfluidized nanoemulsion according to the present invention has improved membrane permeability properties when compared with such free solutions. In one embodiment, the minimal time between administration and intracellular accumulation results in a method of administration having improved efficacy and decreased side effects.

Moreover, as demonstrated herein, the present invention provides botulinum toxin nanoparticle compositions from which botulinum toxin can cross the skin without requiring alteration or disruption of skin structures. For example, commercially available technologies for transdermal administration of biologically active agents traditionally require chemical, physical, electrical or other disruption of at least the outer layer of skin. Such disruption can cause irritation, undesirable medical side-effects, and/or unwanted aesthetic outcomes. The present invention provides botulinum toxin nanoparticle compositions that, when administered to skin, do not significantly or noticeably irritate the skin and/or erode the stratum corneum, and yet allow botulinum toxin to permeate the skin to have its biological effects.

As with proteins generally, the biological activities of the botulinum toxins (which are intracellular peptidases) can be affected by changes in three dimensional conformation. Thus, botulinum toxin type A can be detoxified by heat, various chemicals, surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, solution preparations of the toxin must be formulated with a stabilizing agent, such as albumin.

As noted above, the present invention provides stabilized preparations of botulinum toxin. Notwithstanding the additional stability that may be imparted by the inventive formulation itself, in some embodiments of the invention, use of additional stabilizers is contemplated. For example, in some embodiments, at least one additional protein is used together with the botulinum toxin. In some embodiments, this additional protein comprises albumin. In some embodiments, this additional protein comprises one or more of the proteins naturally found in a botulinum toxin complex. Indeed, in some embodiments of the invention, a complete botulinum toxin complex is employed. In some such embodiments, albumin is also utilized. Thus, in some embodiments, the present invention provides a botulinum microfluidized nanoemulsion comprising albumin.

In some embodiments of the present invention, the botulinum toxin utilized is BOTOX®. BOTOX® consists of a purified botulinum toxin type A complex, albumin and sodium chloride packaged in sterile, vacuum-dried form.

The botulinum toxin type A present in BOTOX® is made from a culture of the Hall strain of *Clostridium botulinum* grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. BOTOX® can be reconstituted with sterile, non-preserved saline prior to intramuscular injection. Each vial of BOTOX® contains about 100 units (U) of Clostridium botulinum toxin type A purified neurotoxin complex, 0.5 milligrams of human serum albumin, and 0.9 milligrams of sodium chloride in a sterile, vacuum-dried form without a preservative.

Currently, BOTOX® is usually reconstituted with 0.9% sodium chloride for administration by injection. Since BOTOX® can be denatured by bubbling or similar violent agitation, the diluent is gently injected into the vial. BOTOX®, as a free solution, is recommended to be administered within four hours after reconstitution. Further, between reconstitution and injection, it is further recommended that reconstituted BOTOX® be stored in a refrigerator (i.e., for example, between 2° to 8° C.). Reconstituted BOTOX® is clear, colorless and free of particulate matter.

It has been reported that BOTOX® has been used in clinical settings as follows:

(1) about 75-125 units of BOTOX® per intramuscular injection (multiple muscles) to treat cervical dystonia;
(2) 5-10 units of BOTOX® per intramuscular injection to treat glabellar lines (brow furrows) (5 units injected intramuscularly into the procerus muscle and 10 units injected intramuscularly into each corrugator supercilii muscle);
(3) about 30-80 units of BOTOX® to treat constipation by intrasphincter injection of the puborectalis muscle;
(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.
(5) to treat strabismus, extraocular muscles have be in injected intramuscularly with between about 1-5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:
  (a) flexor digitorum profundus: 7.5 U to 30 U
  (b) flexor digitorum sublimus: 7.5 U to 30 U
  (c) flexor carpi ulnaris: 10 U to 40 U
  (d) flexor carpi radialis: 15 U to 60 U
  (e) biceps brachii: 50 U to 200 U
  Each of the five indicated muscles has been injected at the same treatment session, so that the patient receives from 90 U to 360 U of upper limb flexor muscle BOTOX® by intramuscular injection at each treatment session.
(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

The present invention demonstrates (see, for example, Examples 4 and 5) that an inventive botulinum nanoparticle composition containing BOTOX®, when incorporated into a cream that is applied to the skin for transdermal delivery of the toxin, achieves biological results (i.e., reduction of wrinkles) comparable to those historically observed with injection of a botulinum toxin solution containing approximately the same about of BOTOX®.

The positive clinical responses of botulinum toxin type A has led to interest in other botulinum toxin serotypes. A study of two commercially available botulinum type A preparations (BOTOX® and DYSPORT®) and preparations of botulinum toxins type B and F (both obtained from Wako Chemicals, Japan) has been carried out to determine local muscle weakening efficacy, safety and antigenic potential. Botulinum toxin preparations were injected into the head of the right gastrocnemius muscle (0.5 to 200.0 units/kg) and muscle weakness was assessed using the mouse digit abduction scoring assay (DAS). $ED_{50}$ values were calculated from dose response curves.

Additional mice were given intramuscular injections to determine $LD_{50}$ doses. The therapeutic index was calculated as $LD_{50}/ED_{50}$. Separate groups of mice received hind limb injections of BOTOX® (5.0 to 10.0 units/kg) or botulinum toxin type B (50.0 to 400.0 units/kg), and were tested for muscle weakness and increased water consumption, the later being a putative model for dry mouth. Antigenic potential was assessed by monthly intramuscular injections in rabbits (1.5 or 6.5 ng/kg for botulinum toxin type B or 0.15 ng/kg for BOTOX®). Peak muscle weakness and duration were dose related for all serotypes.

DAS $ED_{50}$ values (units/kg) were as follows: BOTOX®: 6.7, DYSPORT®: 24.7, botulinum toxin type B: 27.0 to 244.0, botulinum toxin type F: 4.3. BOTOX® had a longer duration of action than botulinum toxin type B or botulinum toxin type F. Therapeutic index values were as follows: BOTOX®: 10.5, DYSPORT®: 6.3, botulinum toxin type B: 3.2. Water consumption was greater in mice injected with botulinum toxin type B than with BOTOX®, although botulinum toxin type B was less effective at weakening muscles. After four months of injections 2 of 4 (where treated with 1.5 ng/kg) and 4 of 4 (where treated with 6.5 ng/kg) rabbits developed antibodies against botulinum toxin type B. In a separate study, 0 of 9 BOTOX® treated rabbits demonstrated antibodies against botulinum toxin type A. DAS results indicate relative peak potencies of botulinum toxin type A being equal to botulinum toxin type F, and botulinum toxin type F being greater than botulinum toxin type B. With regard to duration of effect, botulinum toxin type A was greater than botulinum toxin type B, and botulinum toxin type. B duration of effect was greater than botulinum toxin type F. As shown by the therapeutic index values; the two commercial preparations of botulinum toxin type A (BOTOX® and DYSPORT®) are different. The increased water consumption behavior observed following hind limb injection of botulinum toxin type B indicates that clinically significant amounts of this serotype entered the murine systemic circulation. The results also indicate that in order to achieve efficacy comparable to botulinum toxin type A, it is necessary to increase doses of the other serotypes examined Increased dosage, however, can compromise safety. Furthermore, in rabbits, type B was more antigenic than was BOTOX®, possibly because of the higher protein load injected to achieve an effective dose of botulinum toxin type B. *Eur J Neurol* 6(Suppl 4):53-S10 (1999).

As indicated herein, the present invention contemplates use of botulinum toxin of any serotype. Those of ordinary skill in the art will readily be able to assess the appropriateness of a particular serotype for a particular use and, according to the teachings herein, will be able to prepare nanoparticle compositions containing such botulinum toxin. Thus, the present invention provides nanoparticle compositions containing botulinum toxin of any serotype, including compositions containing only botulinum toxin proteins and compositions containing one or other proteins. In some embodiments, such other proteins comprise or consist of albumin; in some embodiments, botulinum toxin complexes are employed.

Commercially available sources of botulinum toxin that may be utilized in accordance with the present invention include, but are not limited to, BOTOX®, DYSPORT® (*Clostridium botulinum* type A toxin hemagglutinin complex with human serum albumin and lactose; Ispen Limited, Berkshire U.K.) and/or MYOBLOC® (an injectable solution consisting of botulinum toxin type B, human serum albumin, sodium succinate, and sodium chloride, pH 5.6, Elan Pharmaceuticals, Dublin, Ireland), etc.

Nanoparticle Compositions

As described herein, the present invention provides, among other things, compositions that nanoparticle compositions including nanoparticle compositions that contain botulinum toxin.

In general, a nanoparticle composition is any composition that includes at least one nanoparticle. Botulinum nanoparticle compositions are nanoparticle compositions that contain botulinum toxin. The botulinum toxin may be encapsulated or completely surrounded by one or more nanoparticles; associated with the nanoparticle interface; and/or adsorbed to the outer surface of one or more nanoparticles. Botulinum toxin may or may not be covalently linked to the nanoparticles and/or nanoparticle compositions; botulinum toxin may or may not be attached to the nanoparticles and/or nanoparticle compositions by adsorption forces.

In some embodiments, inventive nanoparticle compositions have a uniform collection of nanoparticles. For example, in some embodiments, the difference between the minimum diameter and maximum diameter of the nanoparticles in an inventive nanoparticle composition does not exceed approximately 600, 550, 500, 450, 400, 350, 300, 250, 200, 150, 100, 90, 80, 70, 60, 50, or fewer nm.

In some embodiments, particles (e.g., botulinum-toxin-containing particles) within inventive botulinum nanoparticle compositions have diameters that are smaller than about 600, 550, 500, 450, 400, 350, 300, 250, 200, 150, 130, 120, 115, 110, 100, 90, 80 nm, or less.

In some embodiments, particles (e.g., botulinum-toxin-containing particles) within inventive botulinum nanoparticle compositions have diameters within the range of about 10 and about 600 nanometers. In some embodiments, particles within inventive botulinum nanoparticle compositions have diameters within the range of about 10-300, 10-200, 10-150, 10-130, 10-120, 10-115, 10-110, 10-100, or 10-90 nm.

In some embodiments, particles (e.g., botulinum-toxin-containing particles) within inventive botulinum nanoparticle compositions have an average particle size that is under about 300, 250, 200, 150, 130, 120, or 115, 110, 100, or 90 nm. In some embodiments, the average particle size is within the range of about 10-300, 50-250, 60-200, 65-150, 70-130 nm. In some embodiments, the average particle size is about 80-110 nm. In some embodiments, the average particle size is about 90-100 nm.

In some embodiments, a majority of the particles (e.g., botulinum-toxin-containing particles) within inventive compositions have diameters below a specified size or within a specified range. In some embodiments, the majority is more than 50%, 60%, 70%, 75%, 80%, 85%, 90%, 95%, 96%, 97%, 98%, 99%, 99.5%, 99.6%, 99.7%, 99.8%, 99.9% or more of the particles in the composition.

In some embodiments, inventive nanoparticle compositions are substantially free of particles having a diameter in excess of 120 nm. Specifically, in some embodiments, fewer than 50%, of the nanoparticles in inventive nanoparticle compositions have a diameter in excess of 120 nm. In some embodiments, fewer than 25% of the particles have a diameter in excess of 120 nm. In some embodiments, fewer than 20%, 19%, 18%, 17%, 16%, 15%, 14%, 13%, 12%, 10%, 9%, 8%, 7%, 6%, 5%, 4%, 3%, 2%, 1%, 0.5% or less of the particles have a diameter in excess of 120 nm. Furthermore, in some embodiments, the nanoparticles in inventive nanoparticle compositions have diameters within the range of 10-120 nm.

Zeta potential is a measurement of the electric potential at a shear plane. A shear plane is an imaginary surface separating a thin layer of liquid bound to a solid surface (e.g. the surface of inventive nanoparticles) and showing elastic behavior from the rest of liquid (e.g. liquid dispersion medium) showing normal viscous behavior. In some embodiments, inventive nanoparticles have a zeta potential ranging between −50 mV to +50 mV. In some embodiments, inventive nanoparticles have a zeta potential ranging between −25 mV to +25 mV. In some embodiments, inventive nanoparticles have a zeta potential ranging between −10 mV to +10 mV.

Inventive nanoparticle compositions are typically emulsions or dispersions. In some embodiments, the compositions are "oil-in-water" dispersions (i.e., dispersions in which oily particles are dispersed within an aqueous dispersion medium); in some embodiments, the compositions are "water-in-oil" dispersions (i.e., dispersions in which aqueous particles are dispersed within an oily dispersion medium).

In some embodiments, inventive nanoparticle compositions do not require toxic solvents. By contrast, many conventional strategies for inducing formation of nanoparticles in a composition utilize toxic (typically organic) solvents. In some embodiments, inventive nanoparticle compositions do not require polymers. By contrast, many conventional strategies for preparing compositions that contain nanoparticle structures require polymers.

In some embodiments, inventive nanoparticle compositions have better tissue absorption and/or better biocompatibility than other nanoparticle compositions. For example, in some embodiments, inventive nanoparticle compositions have better tissue absorption and/or better biocompatibility than nanoparticle compositions that are not uniform, that utilize one or more toxic (e.g., organic) solvents, and/or that utilize one or more polymers.

In some embodiments, inventive nanoparticle compositions (e.g., botulinum nanoparticle compositions) are stable. In some embodiments of the invention, a stable nanoparticle composition is one for which the average particle size, the maximum particle size, the range of particle sizes, and/or the distribution of particle sizes (i.e., the percentage of particles above a designated size and/or outside a designated range of sizes) is maintained for a period of time. In some embodiments, the period of time is at least about one hour; in some embodiments the period of time is about 5 hours, 10 hours, one (1) day, one (1) week, two (2) weeks, one (1) month, two (2) months, three (3) months, four (4) months, five (5) months, six (6) months, eight (8) months, ten (10) months, twelve (12) months, twenty-four (24) months, or longer. In some embodiments, the period of time is within the range of about one (1) day to twenty-four (24) months, two (2) weeks to twelve (12) months, two (2) months to five (5) months, etc. For example, if a population of nanoemulsion particles is subjected to prolonged storage, temperature changes, and/or pH changes and a majority of the nanoparticles in the population maintain a diameter within a stated range (i.e., for example, between approximately 10-120 nm), the nanoparticle composition is stable. For some such populations, a majority is more than about 50%, 60%, 70%, 80%, 90%, 95%, 96%, 97%, 98%, 99%, 99.5%, 99.6%, 99.7%, 99.8%, 99.9% or more. In some embodiments of the invention, where a nanoparticle composition comprises botulinum toxin and/or at least one other biologically active agent, the nanoparticle composition is considered stable if the concentration of biologically active agent (e.g., botulinum toxin) is maintained in the composition over the designated period of time under a designated set of conditions.

As described herein, inventive nanoparticle compositions are useful in various medical, cosmetic, and nutraceutical applications. Such compositions may be delivered to a subject by any available route including, but not limited to injection, oral delivery, transdermal delivery, etc. In certain embodiments, the compositions are delivered by injection. In certain embodiments, the compositions are delivered transdermally.

It should be noted that inventive botulinum nanoparticle compositions are readily distinguishable from other botulinum-toxin-containing compositions that have been described. For example, Donovan has described a preparation in which botulinum toxin has been incorporated into a lipid vesicle for transdermal delivery (US Publication 2004/0009180). Such vesicles also require the incorporation of an enhancing agent, such as an alcohol, to facilitate the absorption of botulinum toxin through the skin. Donovan also describes a neurotoxin that is incorporated into a transfersome, which are deformable carriers containing lipids and membrane softeners (Hofer et al., 2000, *World J. Surg.*, 24:1187; and U.S. Pat. No. 6,165,500). Donovan specifically describes the preparation of phosphatidyl choline+sodium cholate liposomes incorporating botulinum toxin.

Suvanprakorn et al. have also described suspensions of liposome-encapsulated materials in discrete macro-beads; one of the literally hundreds of compounds that is said to be amendable to encapsulation is "BOTOX®" (US Publication 2004/0224012). Included in contemplated methods of making these multi-lamellar vesicular liposomes are lyophilization/rehydration and organic solution dehydration/aqueous rehydration. These conventional methods of producing liposomes would be expected to produce microparticle-sized vesicles.

Methods of Making Nanoparticle Compositions

In general, inventive nanoparticle compositions (e.g., botulinum nanoparticle compositions) may be prepared by any available method. In some embodiments, nanoparticle compositions are prepared by chemical means. However, chemical means often require toxic (typically organic) solvents; in some embodiments, nanoparticle compositions are prepared in accordance with the present invention without utilizing such solvents.

In certain embodiments of the present invention, nanoparticle compositions are prepared by preparing a premix and subjecting the premix to high shear forces. As used herein, the term "shear force" refers to a force that is parallel to the face of a material, as opposed to a force that is perpendicular to the face of a material.

Any method known in the art can be used to generate high shear forces. In some embodiments, cavitation is used to generate high shear forces. According to the present invention, the use of mechanical energy (i.e., high shear forces) can replace or minimize any requirement to use costly and/or toxic chemical solvents; can increase the speed at which nanoparticles assemble, can increase the yield of nanoparticles generated in a particular mix of components, and/or can greatly reduce the overall cost of preparing nanoemulsion compositions. Furthermore, in those embodiments in which an agent such as a biologically active agent (e.g., botulinum toxin) is incorporated into inventive nanoparticle compositions, the use of high shear force can increase the loading capacity of the nanoparticle as compared to traditional methods of forming nanoparticles. In traditional methods, loading of agents within or on the surface of nanoparticles typically relies on diffusion of the agent to the interior and/or to the surface of the nanoparticle. According to the present invention, the use of high shear force can allow for the manufacture of smaller particles (e.g., on average) and/or a more narrow distribution of particle sizes in a nanoparticle composition.

In some embodiments, high shear forces are achieved by exposure to high pressure, for example by continuous turbulent flow at high pressure, for example about 15,000 psi. In some embodiments, such high pressure is within the range of about 18,000 to about 26,000 psi; in some embodiments, it is within the range of about 20,000 to 25,000 psi.

In some embodiments, high shear force or high pressure may be administered by cavitation or high pressure homogenization.

In some embodiments, high shear force may be administered by passage through an instrument such as, for example, a Microfluidizer® Processor (Microfluidics Corporation/MFIC Corporation) or other like device. Microfluidizer® Processors provide high pressure and a resultant high shear rate by accelerating the product through microchannels to a high velocity for size reduction to the nanoscale range. The fluid is split in two and is pushed through microchannels with typical dimensions in the order of 75 microns at high velocities (in the range of 50-300 m/s). As the fluid exits the microchannels it forms jets which collide with jets from opposing microchannels. In the channels the fluid experiences high shear (up to $10^7$ l/s) which is orders of magnitude higher than that of conventional technologies. Jet collisions result in mixing in submicron level. Therefore, high shear and impact are responsible for particle size reduction and mixing of multiphase fluids in the Microfluidizer® technology.

More generally, a microfluidizer may be any device that powers a single acting intensifier pump. The intensifier pump amplifies the hydraulic pressure to a selected level which, in turn, imparts that pressure to the product stream. As the pump travels through its pressure stroke, it drives the product at constant pressure through the interaction chamber. Within the interaction chamber are specially designed fixed-geometry microchannels through which the product stream will accelerate to high velocities, creating high shear and impact forces that can generate a uniform nanoparticle composition (e.g., nanoemulsion) as the high velocity product stream impinges on itself and on wear-resistant surfaces.

As the intensifier pump completes its pressure stroke, it reverses direction and draws in a new volume of product. At the end of the intake stroke, it again reverses direction and drives the product at constant pressures, thereby repeating the process.

Upon exiting the interaction chamber, the product flows through an onboard heat exchanger which regulates the product to a desired temperature. At this point, the product may be recirculated through the system for further processing or directed externally to the next step in the process (U.S. Pat. Nos. 4,533,254; and 4,908,154).

In some embodiments of the present invention, a sample is "microfluidized" through exposure to high shear forces for a period of time less than about 10 minutes. In some embodiments, the period of time is less than about 9, 8, 7, 6, 5, 4, 3, 2, or 1 minute(s). In some embodiments, the period of time is within the range of about 1-2 minutes or less; in some embodiments, the period of time is about 30 seconds.

In some embodiments of the invention, a sample is "microfluidized" through a single exposure to high shear forces; such embodiments are referred to herein as "single pass" microfluidization.

The present invention encompasses the recognition that subjecting a premix to high shear forces can generate a nanoparticle composition, and in particular can generate a uniform nanoparticle composition.

In general, the premix from which inventive nanoparticle compositions are prepared through the application of high shear force is expected to contain at least two immiscible materials, one of which will constitute the dispersion medium (i.e., the liquid medium in which particles (e.g., nanoparticles) are dispersed in the ultimate nanoparticle composition). An "oil-in-water" dispersion is one in which oily particles are dispersed within an aqueous dispersion medium. A "water-in-oil" dispersion is one in which aqueous particles are dispersed within an oily dispersion medium. Those of ordinary skill in the art will appreciate that a dispersion can be formed from any two immiscible media and is not limited strictly to combinations of aqueous and oily media. The term "dispersion medium" therefore applies broadly to any dispersion medium notwithstanding that it is common to refer to "aqueous" and "oily" categories.

Thus, in some embodiments of the invention, the premix will contain an aqueous dispersion medium and an oily medium that becomes dispersed in nanoparticle form in the dispersion medium; in some embodiments of the invention, the premix contains an oily dispersion medium and an aqueous medium that becomes dispersed in nanoparticle form in the oily dispersion mediums.

Those of ordinary skill in the art will be well aware of suitable aqueous media that can be used as dispersion media or as media to be dispersed in accordance with the present invention. Representative such aqueous media include, for example, water, saline solutions (including phosphate buffered saline), water for injection, short chain alcohols, 5% dextrose, Ringer's solutions (lactated Ringer's injection, lactated Ringer's plus 5% dextrose injection, acylated Ringer's injection), Normosol-M, Isolyte E, and the like, and combinations thereof.

Those of ordinary skill in the art will also be well aware of suitable oily media that can be used as dispersion media or as media to be dispersed in accordance with the present invention. Representative such oily media include, for example, saturated and unsaturated almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils; butyl stearate; caprylic triglyceride; capric triglyceride; cyclomethicone; diethyl sebacate; dimethicone 360; isopropyl myristate; mineral oil; octyldodecanol; oleyl alcohol; silicone oil; and combinations thereof.

In addition to the two immiscible media, a premix according to the present invention may include, for example, one or more biologically active agents (e.g., botulinum toxin) and/or one or more surfactants or emulsifying agents. Suitable such surfactants or emulsifying agents include, but are not limited to, phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid monoglycerides; fatty acid diglycerides; fatty acid amides; sorbitan trioleate (Span 85) glycocholate; sorbitan monolaurate (Span 20); polysorbate 20 (Tween-20); polysorbate 60 (Tween-60); polysorbate 65 (Tween-65); polysorbate 80 (Tween-80); polysorbate 85 (Tween-85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; poly(ethylene glycol)400-monostearate; phospholipids; synthetic and/or natural detergents having high surfactant properties; deoxycholates; cyclodextrins; chaotropic salts; ion pairing agents; and combinations thereof. The surfactant component may be a mixture of different surfactants. These surfactants may be extracted and purified from a natural source or may be prepared synthetically in a laboratory. In a preferred embodiment, the surfactants are commercially available.

In some embodiments of the present invention, all of the components present in the final nanoparticle composition are present in the premix and are subjected to high shear force to produce the nanoparticle composition. In some embodiments of the present invention, one or more of the components that are present in the final nanoparticle composition is/are missing from the premix or is/are present in the premix in a smaller amount than in the final nanoparticle composition. That is, in some embodiments of the present invention, one or more materials are added to the nanoparticle composition after the premix is subjected to high shear force.

In certain embodiments of the invention, the premix is prepared as a solution prior to application of high shear force. In particular, for nanoparticle compositions that include at least one biologically active agent (e.g., botulinum toxin), it is often desirable for the biologically active agent to be dissolved in the premix before the high shear force is applied. Thus, in many embodiments, the biologically active agent is soluble in at least one of the media (or in a combination of media utilized in the premix). In some embodiments of the invention, such dissolution requires heating; in other embodiments it does not.

In some embodiments of the present invention, the premix components may assemble into particles before the application of high shear force. At least some of such particles may be microparticles or even nanoparticles. In some embodiments, an inventive nanoparticle composition is prepared from a premix, wherein the premix is selected from the group comprising a suspension or a microemulsion. In some embodiments, however, particle structures do not form in the premix before application of high shear force.

In certain embodiments of the invention, relative amount of premix components are selected or adjusted to generate nanoparticles having desired characteristics. In some embodiments, the premix comprises oil and surfactant at a ratio ranging between 0.5-10. In some embodiments, the ratio of oil to surfactant is approximately 0.5:1, 1:1, 2:1, 3:1, 4:1, 5:1, 6:1, 7:1, 8:1, 9:1 or 10:1. In some embodiments, the ratio of surfactant to oil is approximately 0.5:1, 1:1, 2:1, 3:1, 4:1, 5:1, 6:1, 7:1, 8:1, 9:1 or 10:1. In some embodiments, the premix comprises oil and surfactant at a ratio ranging between 0.5-2. In some embodiments, the ratio of oil to surfactant is approximately 0.5:1, 1:1, or 2:1. In some embodiments, the ratio of surfactant to oil is approximately 0.5:1, 1:1, or 2:1. In certain embodiments, the ratio of oil to surfactant is approximately 1:1.

In some embodiments, the percent of oil in the premix ranges between 0%-30%. In some embodiments the percent of oil in the premix is 1%, 2%, 3%, 4%, 5%, 6%, 7%, 9%, 10%, 11%, 12%, 13%, 14%, 15%, 16%, 17%, 18%, 19%, 20%, 21%, 22%, 23%, 24%, 25%, 26%, 27%, 28%, 29% or 30%. In some embodiments the percent of oil is approximately 8%. In some embodiments the percent of oil is approximately 5%.

In some embodiments, the percent of surfactant in the premix ranges between 0%-30%. In some embodiments the percent of surfactant in the premix is 1%, 2%, 3%, 4%, 5%, 6%, 7%, 9%, 10%, 11%, 12%, 13%, 14%, 15%, 16%, 17%, 18%, 19%, 20%, 21%, 22%, 23%, 24%, 25%, 26%, 27%, 28%, 29% or 30%. In some embodiments the percent of surfactant approximately 8%. In some embodiments the percent of surfactant is approximately 5%.

In some embodiments, the nanoparticle composition does not contain more than one oil. In some embodiments, the nanoparticle composition may comprise two or more oils. In some embodiments, the nanoparticle composition does not contain more than one surfactant. In some embodiments, the nanoparticle composition may comprise two or more surfactants.

In some embodiments, the nanoparticle composition consists essentially of water, an oil, a surfactant, and a botulinum toxin. In some embodiments, the nanoparticle composition consists essentially of water, an oil, a surfactant, at least one botulinum toxin, and at least one substance used to produce and/or preserve the nanoparticle composition (e.g. proteins, salts, etc.).

In some embodiments, the nanoparticle composition consists of water, an oil, a surfactant, and a botulinum toxin. In some embodiments, the nanoparticle composition consists of water, an oil, a surfactant, at least one botulinum toxin, and at least one substance used to produce and/or preserve the nanoparticle composition (e.g. proteins, salts, etc.).

Methods of Administering Nanoparticle Compositions

The present invention provides methods of delivering nanoparticle compositions (e.g., botulinum nanoparticle compositions) for various applications including, for example, cosmetic, nutraceutical, and medical applications. Such nanoparticle compositions may include one or more biologically active agents. In many embodiments, the nanoparticle compositions include botulinum toxin.

In some embodiments, the present invention contemplates methods of delivering inventive nanoparticle compositions including, but not limited to transdermal, intramuscular, or subcutaneous routes of administration. These routes of administration are particularly favored for formulations (e.g., certain botulinum toxin nanoparticle compositions) that are intended to have a localized effect. Subsequent tissue absorption of the formulation's ingredients, however, is not always predictable.

In some embodiments of the present invention, inventive formulations may be encapsulated for example using lipid-based carriers, e.g., to facilitate entry into cells. Lipid-based carrier efficacies, however, may be dependent upon; i) lipid composition (i.e., for example, molecular size and charge); ii) the structure (e.g., molecular size and pH ionization) of any biologically active agent or other entity included in the composition; and iii) the overall health of the subject. The present invention contemplates compositions and methods related to uniform microfluidized nanoemulsions comprising either lipid-based carriers thereby improving the bioavailability of cosmeceuticals (i.e., for example, botulinum toxins).

The present invention specifically provides methods of administering botulinum toxin, and particularly of administering botulinum toxin nanoparticle compositions, for the treatment of various disorders, diseases, or conditions. Clinical effects of peripheral injection (i.e., intramuscular or subcutaneous), or topically applied transdermal administration, of botulinum toxins are usually seen within one week. The typical duration of symptomatic relief (i.e., for example, flaccid muscle paralysis) from a single intramuscular injection of botulinum toxin type A can be present for up to four months four months or longer; durations of clinical effect following transdermal administration of botulinum toxins according to the present invention can be present for up to four months or longer, depending on the characteristics of the individual subject and/or one the specific formulation of inventive botulinum nanoparticle preparation.

It will be appreciated by those of ordinary skill in the art that botulinum toxin is currently administered almost exclusively by injection, and in particular by injection of a liquid saline solution, usually reconstituted from a lyophilized preparation.

As already discussed herein, botulinum toxin in the context of such preparations is especially vulnerable to instability resulting in a loss of protein and/or loss of protein activity. Such instability is suspected to a result of protein denaturation, degradation, dimerization, and/or polymerization. The most common formulation known to have botulinum stabilizing effects is human albumin. The possible immunological consequences of human-derived albumin have recently been discussed (US Publication 2005/0238667). This publication proposes that recombinant albumin's, saccharide-based stabilizers, and anti-oxidant amino acids may result in botulinum toxins having an improved efficacy relative to native albumin preparations.

As has also already been discussed, BOTOX® (a purified *Clostridium botulinum* toxin type A complex, human serum albumin, and sodium chloride packaged in a sterile vacuum-dried form) is currently reconstituted for injection using sterile normal saline without a preservative (0.9% sodium chloride, injection grade). Specifically, standard injection protocols involve drawing up the proper amount of diluent in the appropriate size syringe. Since BOTOX® is denatured by bubbling or similar violent agitation, the diluent is gently injected into a vial containing a designated amount of lyophilized BOTOX®. For sterility reasons, standard injection protocols involve administering aqueous BOTOX® solutions within four hours after reconstitution.

Although problems with the available botulinum toxin preparations (including stability issues, sterility issues, etc.) have been well known, few improved formulations have been developed. Furthermore, injection remains the standard approach for delivering botulinum toxin, notwithstanding the undesirability of invasive techniques generally, patient discomfort, etc.

The present invention provides improved botulinum toxin compositions (e.g., botulinum toxin nanoparticle compositions), and further provides improved methods of delivering botulinum toxin. In particular, the present invention provides methods of delivering botulinum nanoparticle compositions (by any available route), and further provides methods of delivering botulinum toxin by routes other than injection.

In general, inventive botulinum nanoemulsion compositions may be administered by any available means including, without limitation, parenterally, orally, transdermally, bucally, opthalmically, vaginally, rectally, etc. In certain embodiments, however, the compositions are administered by injection; in some embodiments by subcutaneous injection, in some embodiments by intramuscular injection, in some embodiments by intravenous injection, etc. In certain embodiments, inventive botulinum nanoparticle compositions are administered transdermally.

In certain embodiments, the present invention provides methods of administering botulinum toxin transdermally. Human skin comprises the dermis and the epidermis. The epidermis has several layers of tissue, namely, stratum corneum, stratum lucidum, stratum granulosum, stratum spinosum, and stratum basale (identified in order from the outer surface of the skin inward).

The stratum corneum presents the most significant hurdle in transdermal delivery of medications generally, and presumably of botulinum toxin in particular. The stratum corneum is typically about 10-15 μm thick, and it consists of flattened, keratised cells (corneocytes) arranged in several layers. The intercellular space between the corneocytes is filled with lipidic structures, and may play an important role in the permeation of substances through skin (Bauerova et al., 2001, *European Journal of Drug Metabolism and Pharmacokinetics,* 26:85).

The rest of the epidermis below the stratum corneum is approximately 150 μm thick. The dermis is about 1-2 mm thick and is located below the epidermis. The dermis is innervated by various capillaries as well as neuronal processes.

Transdermal administration of pharmaceuticals generally has been the subject of research in attempt to provide an alternative route of administration of medications without undesirable consequences associated with injections and oral delivery. For example, needles often cause localized pain, and potentially expose patients receiving injections to blood borne diseases. Oral administration often suffers from poor bioavailability of medications due to the extremely acidic environment of the patient's stomach.

Efforts have been made to develop transdermal administration techniques for certain pharmaceuticals in an attempt to overcome these shortcomings by providing noninvasive administration. It is generally desirable with transdermal administration to reduce damage to a patient's skin. Thus, transdermal administration of medication may reduce or eliminate pain associated with injections, reduce the likelihood of blood contamination, and improve the bioavailability of drugs once they are incorporated systemically.

Traditionally, attempts at transdermal administration of medication have been focused in increasing the permeability of the stratum corneum. Some attempts have included using chemical enhancing agents that increase the permeability of molecules through the skin. Some attempts have included using mechanical apparatus to bypass or ablate portions of the stratum corneum. In addition, attempts have included use of ultrasound or iontophoresis to facilitate the permeation of pharmaceuticals through the skin. In most cases, the goal has been to a pharmaceutical agent, typically a small molecule, through the skin, typically so that an agent may pass to the capillary bed in the dermis where the agent may be systemically incorporated into the subject to achieve a therapeutic effect.

Although small molecules have been a major focus of transdermal administration techniques, it is important to note that it appears that large molecules, such as polypeptides, and protein complexes, are also amenable to transdermal administration. Erythropoietin, which is about 48 kD, has also been successfully transdermally administered with the assistance of ultrasound (Mitragotri et al., 1995, Science, 269:850; and U.S. Pat. Nos. 5,814,599 and 6,002,961).

The present invention provides, among other things, methods of administering botulinum toxin transdermally that do not require use of abrasive or other disrupting agents (whether chemical, mechanical, electrical, magnetic, etc.). Rather, the present inventors have surprisingly found that botulinum toxin incorporated into inventive nanoparticle compositions is effectively delivered transdermally without further steps to permeabilize or disrupt the stratum corneum. Use of such agents or steps with inventive botulinum nanoparticle compositions is not necessarily precluded in all embodiments of the present invention, but also is not required.

The present invention therefore provides methods of administering botulinum toxin through the topical application of an inventive botulinum nanoparticle composition. In some embodiments, the inventive botulinum nanoparticle composition is applied directly to the skin and for absorption through the epidermal layers. In some embodiments, the botulinum nanoparticle composition can penetrate the top layer of the skin, including the stratum corneum, dermal pores, and/or dermal glands, without the use of chemical or mechanical skin permeation enhancers or other agents that cause abrasion.

It will be appreciated by those of ordinary skill in the art that inventive compositions for topical administration may have a cosmetic formulation such as skin softener, nutrition lotion type emulsion, cleansing lotion, cleansing cream, skin milk, emollient lotion, massage cream, emollient cream, make-up base, lipstick, facial pack or facial gel, cleaner formulation such as shampoos, rinses, body cleanser, hair-tonics, or soaps, or dermatological composition such as lotions, ointments, gels, creams, patches or sprays.

An inventive composition for topical administration may be formulated and/or administered such that an amount of botulinum toxin between about $10^{-3}$ U/kg and 10 U/kg passes through a patient's skin. In some embodiments, the composition is formulated and/or administered so that between about $10^{-2}$ U/kg and about 1 U/kg transdermally pass through the patient's skin. In some embodiments, the composition is formulated and/or administered so that between about $10^{-1}$ U/kg and about 1 U/kg pass through the patient's skin. In some embodiments, the composition is formulated and/or administered so that between about 0.1 units and about 5 units pass through the patient's skin to a subdermal target.

Those of ordinary skill in the art will appreciate that units herein relate to Units that are biologically equivalent or bioactively equivalent to Units defined by commercial manufacturers of botulinum toxin.

The therapeutic effects of botulinum toxin administered according to the present invention may persist as long as do the effects of injected solution. The effects of such injected solution can persist for up to about 4 months. Furthermore, use of a synthetic polymer carrier that can retain the botulinum toxin so that it is released slowly may prolong the effects for up to about five years (U.S. Pat. No. 6,312,708).

In one embodiment, the present invention provides a topical formulation of botulinum toxin that avoids potential complications including, but not limited to, systemic toxicity or botulism poisoning. In one embodiment, dosages of botulinum toxin (including types A, B, C, D, E, F, or G) can range from as low as about 1 unit to as high as about 20,000 units, with minimal risk of adverse side effects. The particular dosages may vary depending on the condition being treated and therapeutic regime being utilized. For example, treatment of subdermal, hyperactive muscles may require high transdermal dosages (e.g., 1000 units to 20,000 units) of botulinum toxin. In comparison, treatment of neurogenic inflammation or hyperactive sweat glands may require relatively small transdermal dosages (e.g. about 1 unit to about 1,000 units) of botulinum toxin.

One embodiment of the present invention contemplates a pharmaceutical composition comprising a stabilized botulinum toxin for transdermal delivery into a human patient. The botulinum toxin can be selected from the group consisting of botulinum toxin types A, B, $C_1$, D, E, F and G, an isolated and/or purified (i.e. about 150 kD) botulinum toxin, as well as a native or recombinantly made botulinum toxin. The composition can comprise between about 1 unit to about 20,000 units of the botulinum toxin, and the composition can comprises an amount of botulinum toxin sufficient to achieve a therapeutic effect lasting between 1 month and 5 years.

In some embodiments, the present invention provides topical formulations of botulinum toxin (e.g., of botulinum nanoparticle compositions) that allow the botulinum toxin to permeate through a subject's skin without permeating in significant amount through a blood vessel. For example, in some embodiments of the invention, less than about 25%, or even less than about 5% of the botulinum toxin present in the pharmaceutical composition permeates into a blood vessel upon application of an inventive topical and/or transdermal preparation.

Those of ordinary skill in the art will appreciate that inventive compositions that achieve transdermal administration of botulinum toxin may be incorporated into a device such as, for example, a patch.

A variety of transdermal patch structures are known in the art; those of ordinary skill will appreciate that inventive botulinum nanoparticle compositions may readily be incorporated into any of a variety of such structures. In some embodiments, a transdermal patch may further comprise a plurality of needles extending from one side of the patch that is applied to the skin, wherein the needles extend from the patch to project through the stratum corneum of the skin. In some embodiments, the needles do not rupture a blood vessel.

In some embodiments of the present invention, botulinum toxin (e.g., a botulinum nanoparticle composition) can be provided in a depot in the patch so that pressure applied to the patch causes botulinum toxin to be directed out of the patch (optionally through needles) and through the stratum corneum.

In some embodiments of the present invention, a transdermal patch includes an adhesive. Some examples of adhesive patches are well known (for example, see U.S. Pat. Des. 296,006; U.S. Pat. Nos. 6,010,715; 5,591,767; 5,008,110; 5,683,712; 5,948,433; and 5,965,154). Adhesive patches are generally characterized as having an adhesive layer, which will be applied to a person's skin, a depot or reservoir for holding a pharmaceutical agent, and an exterior surface that prevents leakage of the pharmaceutical from the depot. The exterior surface of a patch is typically non-adhesive.

In accordance with the present invention, the neurotoxin is incorporated into the patch so that the neurotoxin remains stable for extended periods of time. For example, the neurotoxin may be present in an inventive botulinum nanoparticle composition. Alternatively or additionally, the neurotoxin may be incorporated into a polymeric matrix that stabilizes the neurotoxin, and permits the neurotoxin to diffuse from the matrix and the patch. The neurotoxin may also be incorporated into the adhesive layer of the patch so that once the patch is applied to the skin, the neurotoxin may diffuse through the skin. In one embodiment, the adhesive layer may be heat activated where temperatures of about 37° C. cause the adhesive to slowly liquefy so that the neurotoxin diffuses through the skin. The adhesive may remain tacky when stored at less than 37° C., and once applied to the skin, the adhesive loses its tackiness as it liquefies. The administration of the toxin is complete once the patch no longer adheres to the skin.

Those of ordinary skill in the art will appreciate that a transdermal patch is but one example of a device with which inventive botulinum nanoparticle compositions may be administered. To give but a few other examples, a device may be employed that allows the composition to be applied without first applying the composition to one's fingers, which may lead to undesirable paralysis of the fingers. Suitable devices include spatulas, swabs, syringes without needles, and adhesive patches. Use of spatulas or swabs, or the like may require the device to be inserted into a container containing the composition. Using syringes may be accomplished by filling the syringe with the composition. The composition may then be topically spread by the spatulas or swabs, or may be expelled from the syringes onto the person's skin.

In many embodiments of the invention, it may be desirable to limit delivery of botulinum toxin to only an intended delivery area. In some embodiments, such limited delivery may be accomplished by utilizing an inventive botulinum nanoparticle composition in an application device that permits application of the composition to a target site on the skin without applying the composition to non-target site areas of the skin. Clearly, a transdermal patch may be utilized to this end. Alternatively or additionally, if botulinum toxin is to be applied topically to only a selected area, other areas may be covered or pre-treated or otherwise protected from exposure.

Chemodenervation Assessment

Chemodenervating agents such as botulinum toxin act on striated muscle to block release of the acetylcholine neurotransmitter from the presynaptic membrane, resulting in varying degrees of effective denervation of the muscle in regions contacted by the chemodenervating agent. This results in an increase in post-synaptic acetylcholinesterase activity and an increase in the population of acetylcholine receptors, effects which occur as a characteristic physiological response to denervation. Thus, the extent of denervation of a muscle can be determined postmortem by sectioning the muscle and staining for acetylcholinesterase activity using the method of Karnovsky (see, e.g. Woolf et al., *The Innervation of Muscle*, Charles Thomas Pub., Springfield, Ill., 1959).

In accordance with the invention, the extent of spread of a given dose of a chemodenervating agent (e.g. botulinum toxin) is used as a measure of the activity of the preparation, and is used to quantify an appropriate dose for topical administration to the skin overlying a muscle and/or muscle group. This permits a physician to confine the action of the chemodenervating agent to a predetermined volume of muscle and to prevent or minimize the spread of the toxin into adjacent muscle tissue.

Any technique available to one of ordinary skill in the art may be used to determine the extent of diffusion and effective denervation of a given dose of a chemodenervating agent within the muscle of an experimental subject. In some embodiments, the extent of muscular denervation can be determined by measuring acetylcholinesterase activity. For example, a given dose of a toxin preparation is administered to the skin overlying a muscle of an experimental subject (e.g. non-human animal). After a period of time, typically three to five weeks, which is required to fully establish the denervation field, the subject is sacrificed, and in order to assess toxin spread of the administered dose, sections are taken about the site of administration, for example, 3, 10, 15, 30, 45, and 60 mm from the site. Each of the sections is stained to determine acetylcholinesterase activity. This permits visualization of the zone or field of effective denervation, which can be determined precisely. In some embodiments, correlation of these data between, for example, small rodents and simians or between the experimental animals and surgically excised human muscle can provide precise information on the extent of denervation a given quantity of chemodenervating agent will induce when administered to a particular area of skin overlying a human muscle and/or muscle group.

Determination of the extent and zone of inhibition of acetylcholine release can be measured by single fiber electromyography (see, e.g., Sanders et al., 1985, *Neurology*, 35:271). Alternatively or additionally, the presence of acetylcholinesterase can be detected by using labeled binding proteins, such as polyclonal or monoclonal antibodies labeled with fluorescein of other fluorescent moiety; colloidal metallic particles; radionuclides; etc.; and/or other remotely detectable substance. Antibodies to acetylcholine receptors or to acetylcholinesterase can be produced using known techniques. Such antibodies can serve as a marker for effective denervation and/or may recognize epitopes which are newly exposed or which remain after binding of the chemodenervating agent to the receptor on the presynaptic motor end plate. In some embodiments, other histological stains may be used, such as hematoxylin, eosin, and masson trichrome.

In some embodiments, the extent of denervation induced by topical administration of a chemodenervating agent to the skin overlying a muscle can be determined by measuring the decrease in muscle fiber thickness (i.e. fiber atrophy) using fiber diameter variation analysis which occurs about the locus after administration of the chemodenervating agent. The change in muscle fiber diameter can be correlated directly to the dose of chemodenervating agent and to acetylcholinesterase activity. In this method, a desired dosage of chemodenervating agent is topically administered to the skin overlying a muscle and/or muscle group, and allowed to spread to form a denervated area within the muscle or muscle group. Once the denervation field has been established (after about two to five weeks), muscle biopsies are taken at various distances from the administration point and the average muscle fiber diameter at each distance is determined. The diameter of the muscle fibers can be measured by various techniques well known in the art. Typically, a computer-aided system (e.g. Bioquant II System) is used which can measure the diameter of muscle fibers obtained from a biopsy and can calculate an average fiber diameter and variation for the sample. Denervation of an area of muscle blocks the release of acetylcholine in the muscle, resulting in decreased contractility and fiber atrophy. The decrease in muscle fiber diameter can be correlated with the degree of denervation, thus the area denervated by a given dose of chemodenervating agent can be accurately determined.

In some embodiments, the extent of denervation induced by topical administration of a chemodenervating agent to the skin overlying a muscle can be determined by monitoring a reflex motion of a limb of a subject. For example, a reflex motion of a mouse limb can be monitored upon holding the mouse by its tail. The degree to which the mouse does not raise its limb is measured using the digital abductor score (DAS score), a four-point scale developed by Aoki (2001, *Toxicon,* 39:1815; and 2002, *Toxicon,* 40:923).

Therapeutic Applications

When chemodenervating agents are administered to a subject at an appropriate dose, because muscles are only partially weakened, enough strength and neural control remain so that a treated muscle still can perform its primary voluntary function. However, if too large of a dose is administered, the muscle can become completely paralyzed. The degree of weakening from denervation can be "titrated" empirically for particular patients by altering the dose, depending on the desired therapeutic effect one is attempting to achieve.

Thus, the present invention provides methods of standardizing chemodenervating agent-derived pharmaceuticals (e.g. botulinum-derived pharmaceuticals).

In some embodiments, the invention provides methods of standardizing chemodenervating agent preparations (e.g. botulinum toxin preparations) with respect to their zone of denervation when topically administered in vivo. This invention relates to a method of standardizing denervating pharmaceuticals and novel dosage forms based thereon which permit medically safe administration in the management of a variety of disease states and injuries characterized by involuntary muscle spasm or hyperactivation.

In some embodiments, the invention provides mechanisms for testing duration of action and diffusion potential in chemodenervating agent-based preparations (e.g. botulinum toxin preparations).

In some embodiments, the invention provides tools for evaluating diffusion potential of various preparations of botulinum-based pharmaceuticals, e.g., various immunotypes, purifications, and formulations.

In some embodiments, the invention provides methods for rapid approximation of the denervating effect of a chemodenervating agent. For example, a denervating effect can be approximated rapidly (e.g., within about 48 hours) using an animal ptosis model. "Ptosis" refers to the downward displacement of an organ, for example, eyelid drooping. In this method, varying dosages of the chemodenervating agent are topically administered to the skin overlying the muscles and/or muscle groups which control eyelid movement. In some embodiments, a known quantity of a chemodenervating preparation is topically administered to the midface of the subject, specifically to the skin overlying the levator palpebral superioris muscle, thereby inducing ptosis in the eyelids of the subject. The degree of ptosis is indicative of the degree of diffusion into the orbit resulting in decreased levator muscle tone and contractility, and thus the extent of denervation induced by the dose administered. Such an assay enables a drug manufacturer to quickly determine an estimate of the potency of a given volume or mass of a particular batch of chemodenervating agent by administering it to the skin overlying a muscle in the vicinity of the eyes of an animal and observing the resulting ptosis. As an alternative or in addition to ptosis, globe prolapse can be observed as an orbital change resulting from diffusion of chemodenervating agent into the orbital musculature. As used herein, the term "globe" refers to the globe of the eye (bulbus oculi). These methods have the advantage that the subject need not be sacrificed, and the results can be evaluated within a relatively short time, e.g., about 48 hours.

Such techniques enable chemodenervating agents to be prepared in various dosage forms and provides nomograms which enable a physician to administer chemodenervating agents (e.g. neurotoxins such as botulinum toxin) for therapeutic purposes responsibly while eliminating or minimizing side effects caused by unwanted chemodenervation agent spread beyond the intended denervation zone. Some degree of paresis and muscle weakening beyond the intended locus of denervating action may nevertheless occur. However, the physician may use the techniques and chemodenervating pharmaceuticals standardized as herein disclosed to tailor doses to the selected site(s) of administration based on his diagnosis determining the affected muscles, and to predict the duration of activity of new formulations in clinical studies. The denervating effect, therefore, can be confined essentially to a given muscle and/or muscle group, despite the observation that the botulinum toxin can spread beyond intervening facial planes and bony structures.

Kits

The invention provides a variety of kits useful for assaying the activity of chemodenervation agents in accordance with the present invention. A kit may comprise one, two, three, or more different substances useful for detecting activity of chemodenervation agents. A kit may comprise any of a number of additional components or reagents in any combination. All of the various combinations are not set forth explicitly but each combination is included in the scope of the invention.

According to certain embodiments of the invention, a kit may include, for example, (i) a substance which detects levels of acetylcholinesterase (ACE) in muscle nerve terminals; and (ii) instructions for administering the substance to a subject in order to assay activity of a chemodenervating agent being tested.

According to certain embodiments of the invention, a kit may include, for example, (i) a substance which detects levels of acetylcholinesterase (ACE) in muscle nerve terminals; (ii) a "standard" chemodenervating agent which has a characteristic effect on ACE levels; and (ii) instructions for administering the substance to a subject in order to assay activity of a chemodenervating agent being tested.

Kits generally include one or more vessels or containers so that some or all of the individual components and reagents may be separately housed. Kits may also include a means for enclosing individual containers in relatively close confinement for commercial sale, e.g., a plastic box, in which instructions, packaging materials such as styrofoam, etc., may be enclosed. An identifier, e.g., a bar code, radio frequency identification (ID) tag, etc., may be present in or on the kit or in or one or more of the vessels or containers included in the kit. An identifier can be used, e.g., to uniquely identify the kit for purposes of quality control, inventory control, tracking, movement between workstations, etc.

EXEMPLIFICATION

The following examples are only intended to provide illustrations of specific embodiments contemplated by the present invention. The examples are not intended in any way to be limiting.

Example 1

Assessment of Biochemical and Physiological Chemodenervation Effects

Experimental data were developed to demonstrate the effectiveness of inventive methods. Data were obtained using a treatment approach employing a topical preparation of botulinum toxin type A, a chemodenervating agent, in a mouse study. In particular, topical application of the botulinum preparation was compared to a control. Botulinum is thought to achieve muscle paralysis through chemodenervation because botulinum is a neurotoxin. Previous studies have reported two methods used to assess the paralytic effects of injected botulinum in mice: 1) a biochemical effect in the muscle tissue that is observed by immunohistochemistry; and 2) a physiological effect of muscle weakness that is observed by examining the movement of the mouse limbs.

Assessment of Biochemical Effect

The biochemical effect was observed by measuring levels of acetylcholinesterase (ACE) in the muscle nerve terminals. An accumulation of ACE is indicative of muscle nerve paralysis. The immunohistochemical score is a measurement of the number of nerve terminals which have been chemodenervated, and exhibit accumulated ACE in immunohistochemical analyses using the Karnovsky histological staining method (1964, *J. Histochem. Cytochem.,* 12:219). One week after treatment, the topical botulinum preparation achieved an immunohistochemical score of $5.0\pm1.0$, which was statistically different from a control score of $1.0\pm0.2$ (P<0.002). By three weeks after treatment, the topical botulinum preparation had a score of $5.7\pm0.8$, which was statistically different from a control of $1.0\pm0.2$ (P<0.024). FIG. 1 presents ACE tissue stain photomicrographs of mouse bicep muscle tissue, for which skin overlying muscles was treated with topical botulinum (FIG. 1A). FIG. 1 presents ACE tissue stain photomicrographs of mouse bicep muscle tissue, for which skin overlying muscles was treated with topical botulinum preparation containing 0.3 U of Botulinum Type A Toxin Complex admixed in a facial cream ("PCCA Vanishing Cream") (FIG. 1A) or with a negative control preparation containing the identical chemical constituents of the botulinum preparation except the Botulinum Type A Toxin Complex admixed with the same facial cream (FIG. 1B). The botulinum-treated (FIG. 1A) and control (FIG. 1B) groups had the same volume of cream applied. FIG. 1A shows positive ACE staining of the nerve terminals (innervating the muscle) demonstrating that this muscle was denervated in the pharmacologically treated muscle. FIG. 1B shows negative ACE staining of the nerve terminals (innervating the muscle) demonstrating that the muscle treated with the control preparation was not denervated.

Assessment of Physiological Effect

The physiological effect was measured by observing a reflex motion of the mouse limb upon holding the mouse by its tail. The degree to which the mouse does not raise its limb is measured using the digital abductor score (DAS score), a four-point scale developed by Aoki (2001, *Toxicon,* 39:1815; and 2002, *Toxicon,* 40:923). At one week after treatment, the topical botulinum preparation achieved a score of $2.8\pm0.3$, compared to a control score of $0.5\pm0.3$ (P<0.001). By three weeks after treatment, the topical botulinum preparation effects were at control levels, as expected by the published literature on injected botulinum (this decrement in Aoki scale in mice has been observed repeatedly with botulinum, which nevertheless has a continued anti-wrinkle effect for several months when used at therapeutic doses in humans).

Example 2

Botulinum Nanoemulsion Formulation

This example presents one embodiment of nanoemulsion prepared by microfluidization comprising botulinum toxin (i.e., for example, BOTOX®).

Figure 2:
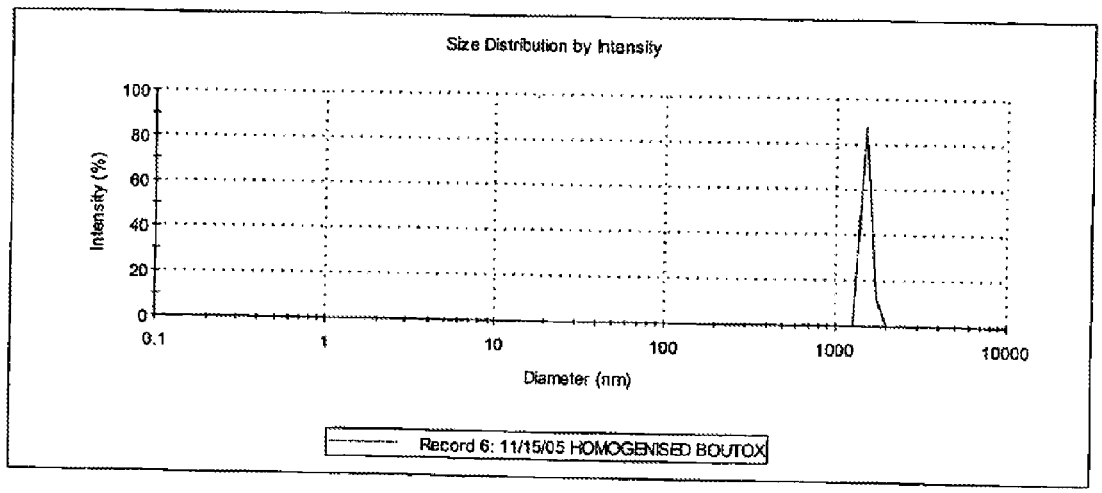
FIG. 2: Particle diameter distributions in formulation of botulinum nanoemulsion. (A) One embodiment of a particle diameter distribution of homogenized botulinum toxin microemulsion; and (B) on embodiment of a particle diameter distribution of a microfluidized botulinum toxin nanoemulsion.
Figure 2:
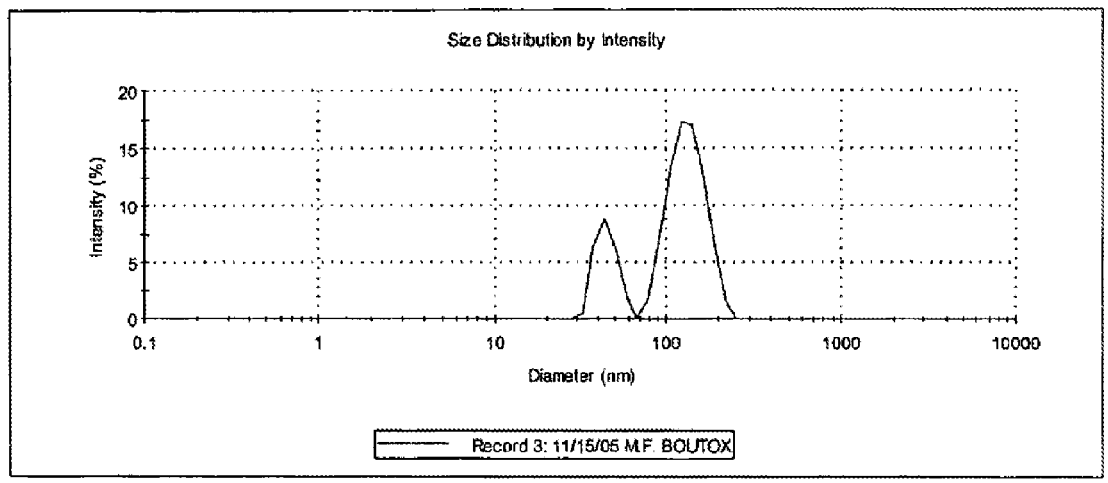

A preparation for microfluidization was made as follows:
1. 5 g of soybean oil and 5 g of Tween 80 were mixed, heating as needed (typically not required) to emulsify the mixture.
2. 100 Units of BOTOX®, incorporated within a human albumin matrix (Allergan, Irvine Calif.), was added to 100 mL of deionized/distilled water and stirred until evenly mixed.
3. Step 1 preparation was added to Step 2 preparation and stirred until evenly mixed.
4. Preparation was homogenized for 1 minute (see resulting particle distributions in Table 1 and FIG. 2A)
5. Single-pass microfluidization procedure at 24,000 psi was performed using a Microfluidizer® Processor.

The resulting nanoemulsion was evaluated for particle size using the Malvern Nano S particle sizer capable of sizing particles between about 0.6 nm-6000 nm. The BOTOX® nanoemulsion preparation had two particle size peaks having an average particle size of 95.33 nm (Table 2 and FIG. 2B).

TABLE 1

Particle Size Distribution of a Homogenized BOTOX ® Microemulsion

|  |  | Diam. (nm) | % Intensity | Width (nm) |
| --- | --- | --- | --- | --- |
| Z-Average: 3391 | Peak 1 | 1512 | 100 | 76.6 |
| PDI: 0.341 | Peak 2 | 0 | 0 | 0 |
| Intercept: 0.5852 | Peak 3 | 0 | 0 | 0 |

TABLE 2

Particle Size Distribution of a Microfluidized BOTOX ® Nanoemulsion

|  |  | Diam. (nm) | % Intensity | Width (nm) |
| --- | --- | --- | --- | --- |
| Z-Average: 95.33 | Peak 1 | 134.2 | 76.49 | 31.03 |
| PDI: 0.252 | Peak 2 | 44.97 | 23.51 | 6.34 |
| Intercept: 0.9659 | Peak 3 | 0 | 0 | 0 |

Example 3

Muscle Relaxant Effect of Injected BOTOX® Nanoemulsions

This example presents one embodiment of BOTOX® nanoemulsions that have comparable efficacy as free solution BOTOX® injections as a saline solution.

The experimental design compared the following two BOTOX® preparations:
1) BOTOX® nanoemulsions, prepared in accordance with Example 1, were injected via intramuscular (IM) injection into the hind leg (gastrocnemius muscle) of Swiss Webster female mice.
2) BOTOX® saline solutions were injected via intramuscular (IM) injection into the hind leg gastrocnemius muscle of Swiss Webster female mice.

The Digit Abduction Score (DAS) assay was used to determine local muscle weakening efficacy (Aoki, 1999). The DAS values were assigned as follows: (0) flat foot, digit spread same as control leg; (1) flat foot, a difference in the width of digit abduction compared to the control leg or two digits touching and the rest spread completely; (2) flat foot, slight space open at tips of all digits or three digits touching; (3) five digits touching if foot is flat, four digits together if foot is curved; (4) curved foot, all five digits touching.

IM injection of BOTOX® nanoemulsion and BOTOX® saline solution were evaluated by DAS seven days under a single-blind protocol. DAS scores of 1-2 were observed for both the botulinum toxin nanoemulsion (3.96 U/5 µl) and botulinum toxin saline solution (3.96 U/5 µl). The control group, which is a blank nanoemulsion, had DAS (0). Each group (botulinum toxin nanoemulsion, saline, and control) was comprised of five (5) animals.

This information proves that microfluidization techniques do not destroy the functional characteristics of botulinum toxin as demonstrated by injection of non-microfluidized botulinum toxin saline solution and that the botulinum toxin nanoemulsions are functionally effective.

Example 4

Muscle Relaxant Effect of Transdermal BOTOX® Nanoemulsions

This example demonstrates the therapeutic efficacy of transdermally applied botulinum nanoemulsions (i.e., for example, a BOTOX® nanoemulsion).

A BOTOX® nanoemulsion (9.9 U/100 µl), prepared in accordance with Example 1, was topically administered to the hind leg gastrocnemius muscle of five (5) Swiss Webster female mice. A control group of five (5) Swiss Webster female mice received an identically prepared nanoemulsion except that BOTOX® was omitted. During the seven days following treatment, DAS scores of 1-2 were observed, scored in accordance with Example 2, for the botulinum toxin nanoemulsion treated group but not in the control group. Aggravation of the skin (e.g. irritation, redness, etc.) was not observed at any time after treatment. The data show that a botulinum toxin nanoemulsion is biologically active upon transdermal administration in a manner similar to conventionally administered botulinum toxin injections.

Example 5

Muscle Relaxant Effects Due to Administration of a Botulinum Nanoemulsion: Controlled Comparison of Standard Injected Botulinum vs. Topical Botulinum Nanoemulsion in Mice This example provided a controlled experiment to demonstrate that application of an inventive topical botulinum nanoemulsion could induce muscle relaxant effects equivalent to a standard injected botulinum preparation (that was not a nanoemulsion).

Method

Thirty-five female Swiss Webster mice were purchased from Charles River at approximately 20 grams of weight. Upon arrival, all animals were acclimated to their cages for one week (group housed 5 mice per cage per Group as defined below) and provided with standard cage bedding and Purina 5001 chow. After one week, Digit Abduction Scoring (DAS) was used to determine local muscle function following application of a BOTOX® nanoemulsion prepared in accordance with Example 1. In the DAS assay, mice were suspended by the tail briefly (10 seconds) to elicit a characteristic startle response in which the animal extended its hind legs and abducts its hind digits. This assay was performed once a week for 3 weeks.

Three treatment preparations were prepared for three treatment groups of mice: 1) BOTOX® in a saline solution for injection, 2) a nanoemulsion containing BOTOX® and 3) a "blank" nanoemulsion containing all the constituents of the BOTOX® nanoemulsion except the BOTOX® that was also processed through the Microfluidizer® Processor in a manner identical to the nanoemulsion containing BOTOX®.

Treatment Paradigms

Group 1 (IM) 15 Mice were injected with 10 U/5 uL of BOTOX®/kg of body weight that was suspended in a saline solution and then injected into the gastrocnemius muscle of the hind leg of the mice.

Group 2 (Topical) 15 Mice were treated topically with 10 U/100 µl of nanoemulsion of BOTOX®/kg of body weight that was applied to the skin of the mice overlying the gastrocnemius muscle of the hind leg.

Group 3 (Control) 15 Mice were treated topically with blank nanoemulsion containing no BOTOX® that was applied to the skin of the mice overlying the gastrocnemius muscle of the hind leg.

Assessment

One week after injection and/or transdermal application, the DAS assay was used to determine potential local muscle weakening effects of treatment. This assay was performed once a week for the next three weeks. Following injection and/or transdermal application of BOTOX® or a control preparation, the varying degrees of digit abduction was scored on a five-point scale (0=normal to 4=maximal reduction in digit abduction and leg extension) by an observer who was masked to treatment.

Results and Conclusion

At one week after treatment, the group of mice (Group #2) treated with the topical botulinum nanoemulsion preparation achieved a score of 2.8+0.3 on the Aoki scale compared to the control group of mice (Group #3) treated with the blank nanoemulsion that had a score of 0.5+0.3 ($P<0.001$). By comparison, those mice (Group #1) injected with botulinum in a saline solution had a score of 3.5+0.3. By three weeks after treatment, both the group of mice treated with the topical botulinum nanoemulsion preparation and those mice injected with botulinum in saline had Aoki scores that were at control levels, as expected by the published literature on injected botulinum. (This decrement in Aoki scale in mice has been observed repeatedly with botulinum, which nevertheless has a continued anti-wrinkle effect for several months when used at therapeutic doses in humans.) Furthermore, aggravation of the skin (e.g. irritation, redness, etc.) was not observed at any time after treatment.

In sum, this controlled data suggest strongly that the topical botulinum nanoemulsion preparation delivered a comparable biological effect to injected botulinum.

Example 6

Administration of Botulinum Nanoparticle Composition to a Human Subject to Relieve Wrinkles An inventive topical botulinum nanoemulsion was prepared and applied to a person with significant forehead wrinkles to determine if it could be effective in relaxing the muscles in the forehead that generated those wrinkles (in much the same manner that would be expected from the administration of botulinum suspended in a simple saline solution that was injected into those muscles).

Methods

A botulinum nanoemulsion was made employing the following steps:
1. Stir 800 mg of soybean oil and 800 mg of Tween 80 in a sterile vial for 5 minutes
2. Add 8.4 mL 0.9% saline with 4500 units of an approved botulinum type A toxin pharmaceutical. Stir for 20 minutes
3. Homogenize sample for 1 minute
4. Stir sample for 20 minutes
5. Microfluidize once at 23,000 psi The nanoemulsion was added to an equal volume of skin cream (Base PCCA Vanishing Cream Light) and was vortexed into a uniform cream.

A patient who had significant horizontal wrinkles over his forehead, representing overactivity of his frontalis muscles, was selected for treatment. This patient had had never been treated with a botulinum product or a dermal filler product. The patient was assessed prior to treatment by a board-certified plastic surgeon using a 4-point wrinkle scale, with a score of "1" equal to "no wrinkle" and a score of "4" equal to significant wrinkle. The patient was assessed using this scale when his face was "At Rest" and when he attempted to create maximal wrinkles by contracting his frontalis muscles which was achieved by attempting to maximally elevate his eyebrows ("Maximal Brow Elevation").

Figure 3A:
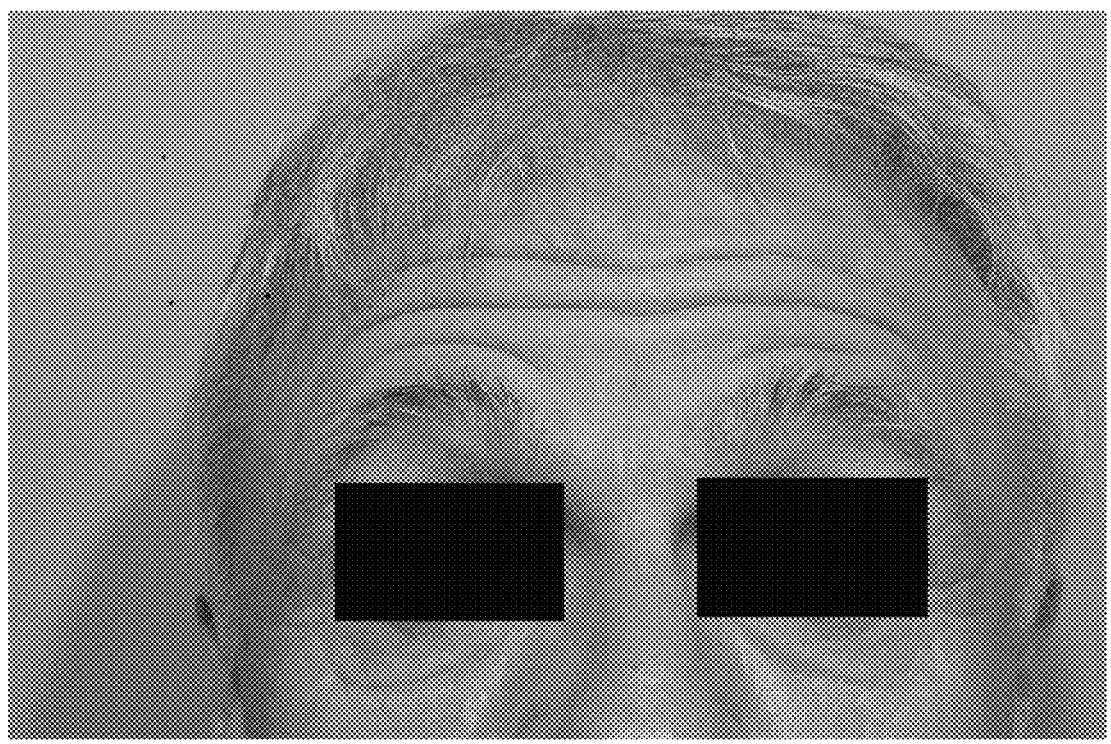
FIG. 3: A patient attempting maximal brow elevation prior to (Panel A) and two weeks after (Panel B) topical administration of an inventive composition comprising a botulinum nanoparticle composition.

This patient had a score of 4 at rest and 4 on maximal brow elevation. He demonstrated excellent mobility of being able to contract the frontalis muscles. The patient was photographed using a digital SLR camera as well as digital video, both At Rest and when asked to perform a Maximal Brow Elevation (FIG. 3A, maximal brow elevation prior to treatment).

The patient was asked not to use any facial make-up or sun-screen on the day of treatment but wash his face prior to coming to the office with Ivory Soap. When at the office, 0.6 CC of the nanoemulsion cream (as prepared in Example 1) was applied to the patient's forehead over the distribution of his frontalis muscles by the plastic surgeon. The cream was applied to the patient's forehead skin by a pipette and rubbed into the skin by the surgeon using his finger (covered by a plastic glove) until the cream was no longer visible by the surgeon. The patient was observed at the physician's office for three hours. He was asked not to touch his forehead for 12 hours and then to wash it off with Ivory Soap and water. The patient was the observed on follow-up after 1 day and then at 1, 2, 4, 8, and 12 weeks. On follow-up visits, the patient's wrinkles At Rest and at Maximal Brow Elevation were assessed by the physician. As well, the physician repeated standardized digital still photographs and video.

Results

Figure 3B:

By the first week after treatment, the patient was unable to contract his forehead muscles as evidenced by an inability to lift his brow on requested Maximal Brow Elevation (FIG. 3B). His wrinkle score was 2 At Rest and 2 on Maximal Brow Elevation. The physician's clinical assessment was that the treatment had induced a complete paralysis of the treated muscles that was equivalent to treatments he had performed on other patient's using injections of botulinum toxin in a similar treatment area. The patient had a slight restoration of brow mobility by Week 8 but continued to have a significant reduction in his brow mobility at Week 12 of observation.

The patient was able to move his other facial muscles under areas of skin not treated and no side-effects were observed by the plastic surgeon, including no changes to the skin immediately after treatment or in any follow-up visit. Likewise, the patient reported no side-effects, including any changes to his skin (e.g. irritation, redness, etc.) at any time after treatment.

Conclusion

In sum, this experiment strongly suggests that the topical botulinum nanoemulsion preparation delivered a significant biological and clinical effect that was assessed by the plastic surgeon to be comparable in clinical efficacy to what would have been expected for following a standard treatment of injected botulinum (in a simple saline solution) for this patient.

Example 7

Further Botulinum Nanoparticle Composition Formulations

A variety of different botulinum nanoparticle compositions were prepared in accordance with Example 1 except that in some cases, there were differences in the equipment used, the pressure applied, the amount of botulinum added, and the volume of nanoparticle composition prepared, which may account for the variability of the sizes observed. The following average particle size and distributions were observed (Table 3):

TABLE 3

Particle Size Distribution of Microfluidized BOTOX ® Nanoemulsions

| Distribution Threshold (nm) | Mean Particle Size (nm) | | | | | | Average |
|---|---|---|---|---|---|---|---|
| | 76.8 | 91.5 | 94.2 | 95.3 | 97.9 | 112.4 | 95 |
| % above 120 | 36.4 | 48.6 | 47.6 | 54.7 | 50.7 | 53.8 | 49 |
| % above 130 | 21.0 | 37.8 | 35.5 | 37.3 | 40.8 | 45.2 | 36 |
| % above 150 | 9.1 | 27.4 | 24.8 | 20.3 | 31.4 | 36.8 | 25 |
| % above 200 | 2.8 | 16.1 | 10.3 | 1.5 | 15.7 | 21.7 | 11 |
| % above 300 | 0.0 | 0.6 | 4.5 | 0.0 | 3.6 | 9.6 | 3 |

Example 8

Relationship of Pressure Applied to Average Particle Size Achieved

A premix formulation was prepared as described in Example 1 (except for the absence of botulinum toxin) and was split into 4 100 ml aliquots, A-D, each of which was passed through a Microfluidizer® at a different pressure, resulting in a different average particle size, as indicated below in Table 4:

TABLE 4

Particle Sizes of BOTOX ® Nanoemulsions Microfluidized at Different Pressures

| Preparation | Pressure (psi) | Average Particle Size (nm) |
| --- | --- | --- |
| A | 3,500 | 142 nm |
| B | 10,000 | 107 nm |
| C | 17,000 | 94 nm |
| D | 24,000 | 89 nm |

Equivalents and Scope

The foregoing has been a description of certain non-limiting preferred embodiments of the invention. Those skilled in the art will recognize, or be able to ascertain using no more than routine experimentation, many equivalents to the specific embodiments of the invention described herein. Those of ordinary skill in the art will appreciate that various changes and modifications to this description may be made without departing from the spirit or scope of the present invention, as defined in the following claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise. For example, it is to be understood that any of the compositions of the invention can be used for inhibiting the formation, progression, and/or recurrence of adhesions at any of the locations, and/or due to any of the causes discussed herein or known in the art. It is also to be understood that any of the compositions made according to the methods for preparing compositions disclosed herein can be used for inhibiting the formation, progression, and/or recurrence of adhesions at any of the locations, and/or due to any of the causes discussed herein or known in the art. In addition, the invention encompasses compositions made according to any of the methods for preparing compositions disclosed herein.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Any embodiment, element, feature, application, or aspect of the compositions and/or methods of the invention (e.g., any chemodenervation agent; any method of chemodenervation assessment; any therapeutic application for chemodenervation assessment; etc.), can be excluded from any one or more claims. For purposes of brevity, all of the embodiments in which one or more elements, features, purposes, or aspects are excluded are not set forth explicitly herein.

I claim:

1. A method of measuring the denervating activity of a chemodenervating agent comprising:
   administering the chemodenervating agent to the skin surface overlying a muscle or muscle group of a subject, wherein the chemodenervating agent is formulated as a nanoparticle composition;
   permitting the chemodenervating agent to diffuse within the muscle or muscle group, thereby establishing a denervation field; and
   determining the extent of the denervation field induced by the administered chemodenervating agent within the muscle or muscle group.

2. The method of claim 1, wherein the chemodenervating agent is botulinum toxin.

3. The method of claim 2, wherein the botulinum toxin selected from the group consisting of botulinum toxin serotypes A, B, $C_1$, $C_2$, D, E, F, and G.

4. The method of claim 1, wherein the chemodenervating agent is botulinum toxin serotype A.

5. The method of claim 1, wherein the step of determining the extent of the denervation field is performed by measuring inhibition of acetylcholine release in muscle groups underneath the site of topical administration.

6. The method of claim 5, comprising determining the local concentration of acetylcholinesterase in regions of muscle located underneath the site of topical administration at the time of administration.

7. The method of claim 6, wherein the local concentration is determined by histochemical estimation of acetylcholinesterase enzyme activity.

8. The method of claim 1, wherein the step of determining the extent of the denervation field is performed by determining the extent of inhibition of muscle stimulation in regions of the muscle spaced apart from underneath the site of topical administration by electrophysiologic testing.

9. The method of claim 8, comprising determining the extent of effective muscular stimulation by single fiber electromyography.

10. The method of claim 1, wherein the step of determining the extent of the denervation field is performed by determining the density of acetylcholine receptors or acetylcholinesterase in regions of the muscle located underneath the site of topical administration at the time of administration.

11. The method of claim 10, wherein the density of said acetylcholine receptors or acetylcholinesterase is determined by binding labeled antibodies to the receptors or acetylcholinesterase.

12. The method of claim 10 or 11, wherein the intensity and pattern of acetylcholine receptors or acetylcholinesterase staining is determined by qualitative or quantitative evaluation using a scoring system through the manual examination of the tissue or image of the tissue.

13. The method of claim 10 or 11, wherein the intensity and pattern of acetylcholine receptors or acetylcholinesterase staining is determined by qualitative or quantitative evaluation using a scoring system of 0-4 through the manual examination of the tissue or image of the tissue.

14. The method of claim 10 or 11, wherein the intensity and pattern of said acetylcholine receptors or acetylcholinesterase staining is determined by qualitative or quantitative evaluation using a scoring system using an automated or semi-automated examination of the tissue or image of the tissue.

15. The method of claim 10 or 11, wherein the intensity and pattern of said acetylcholine receptors or acetylcholinesterase staining is determined by qualitative or quantitative evaluation using a scoring system of 0-4 using an automated or semi-automated examination of the tissue or image of the tissue.

16. The method of claim 10 or 11, wherein the intensity and pattern of said acetylcholine receptors or acetylcholinesterase staining is determined by qualitative or quantitative evaluation using a scoring system using computer-assisted examination of the tissue or image of the tissue.

17. The method of claim 10 or 11, wherein the intensity and pattern of said acetylcholine receptors or acetylcholinesterase staining is determined by qualitative or quantitative evaluation using a scoring system of 0-4 using computer-assisted examination of the tissue or image of the tissue.

18. The method of claim 1, wherein the step of determining the extent of the denervation field is performed by observing a reflex motion of a limb of the subject.

19. The method of any one of claims 1-11, wherein the subject is a human.

20. The method of claim 1, wherein the nanoparticle composition can penetrate skin without the use of chemical permeation enhancers or abrasives.

21. The method of claim 1, wherein the nanoparticle composition can penetrate skin without the use of mechanical permeation enhancers or abrasives.

22. The method of claim 1, wherein the nanoparticle composition can penetrate skin without altering or changing the skin.

23. The method of claim 1, wherein the nanoparticle composition is a uniform nanoparticle composition.

24. A method of measuring the denervating activity of chemodenervating agent comprising: administering the chemodenervating agent to the skin in a nanoparticle formulation comprising a nanoemulsion characterized in that a majority of its particles have diameters between approximately 10 and approximately 300 nanometers, wherein said nanoemulsion comprises at least one botulinum toxin, wherein the skin to which the agent is administered overlies a muscle or muscle group of a subject;

permitting the chemodenervating agent to diffuse within the muscle or muscle group, thereby establishing a denervation field; and determining the extent of the denervation field induced by the administered chemodenervating agent within the muscle or muscle group.

* * * * *